United States Patent
Yu et al.

(10) Patent No.: US 9,725,736 B2
(45) Date of Patent: Aug. 8, 2017

(54) MUTANT GIBBERELLIN 2-OXIDASE GENES AND USES THEREOF

(71) Applicant: Academia Sinica, Taipei (TW)

(72) Inventors: Su-May Yu, Taipei (TW); Shuen-Fang Lo, Taichung County (TW); Liang-Jwu Chen, Taichung (TW); Tuan-Hua David Ho, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/648,053

(22) PCT Filed: Nov. 29, 2013

(86) PCT No.: PCT/US2013/072487
§ 371 (c)(1),
(2) Date: May 28, 2015

(87) PCT Pub. No.: WO2014/085763
PCT Pub. Date: Jun. 5, 2014

(65) Prior Publication Data
US 2016/0046956 A1    Feb. 18, 2016

Related U.S. Application Data

(60) Provisional application No. 61/730,737, filed on Nov. 28, 2012.

(51) Int. Cl.
*C12N 15/82* (2006.01)
*C12N 9/02* (2006.01)

(52) U.S. Cl.
CPC ....... *C12N 15/8297* (2013.01); *C12N 9/0071* (2013.01); *C12N 15/8261* (2013.01); *C12N 15/8267* (2013.01); *C12N 15/8269* (2013.01); *C12N 15/8271* (2013.01); *C12N 15/8273* (2013.01); *C12Y 114/11013* (2013.01)

(58) Field of Classification Search
None
See application file for complete search history.

(56) References Cited

U.S. PATENT DOCUMENTS

2009/0313725 A1    12/2009    Yu et al.
2010/0095406 A1    4/2010    Yu et al.

OTHER PUBLICATIONS

Hsieh et al., Functional Study of Rice GA 2-oxidase I. Characterization of Rice GA2ox2 and Its T-DNA Activation Mutant M43852 II. Functional Study of the Conserved Motifs in C20 Type Osga2ox6. Thesis. Published Nov. 28, 2011; Foreign Summary, 4 pages.*
Berg et al, Biochemistry, 5th Edition, New York, W. H. Freeman, 2002, Table 5.4.*
GenBank Submission; NIH/NCBI, Accession No. AK107142.1, Kikuchi et al., Oryza Sativa Japonica Group cDNA Clone:002-124-D04, Full Insert Sequence, Dec. 4, 2008, 3 pages.
Hsieh et al., Functional Study of Rice GA 2-oxidase I. Characterization of Rice GA2ox2 and Its T-DNA Activation Mutant M43852 II. Functional Study of the Conserved Motifs in C20 Type Osga2ox6. Thesis. Published Nov. 28, 2011, Foreign Summary, 4 pages.

* cited by examiner

*Primary Examiner* — Eileen O Hara
(74) *Attorney, Agent, or Firm* — Wolf, Greenfield & Sacks, P.C.

(57) ABSTRACT

The present invention relates to mutant gibberellin 2-oxidase (GA2ox) genes and uses thereof. In particular, the effective mutations disclosed herein can reduce GA2ox enzymatic activity to different extents, leading to various degrees of GA deficient yet beneficial agronomic traits in transgenic plants.

18 Claims, 13 Drawing Sheets

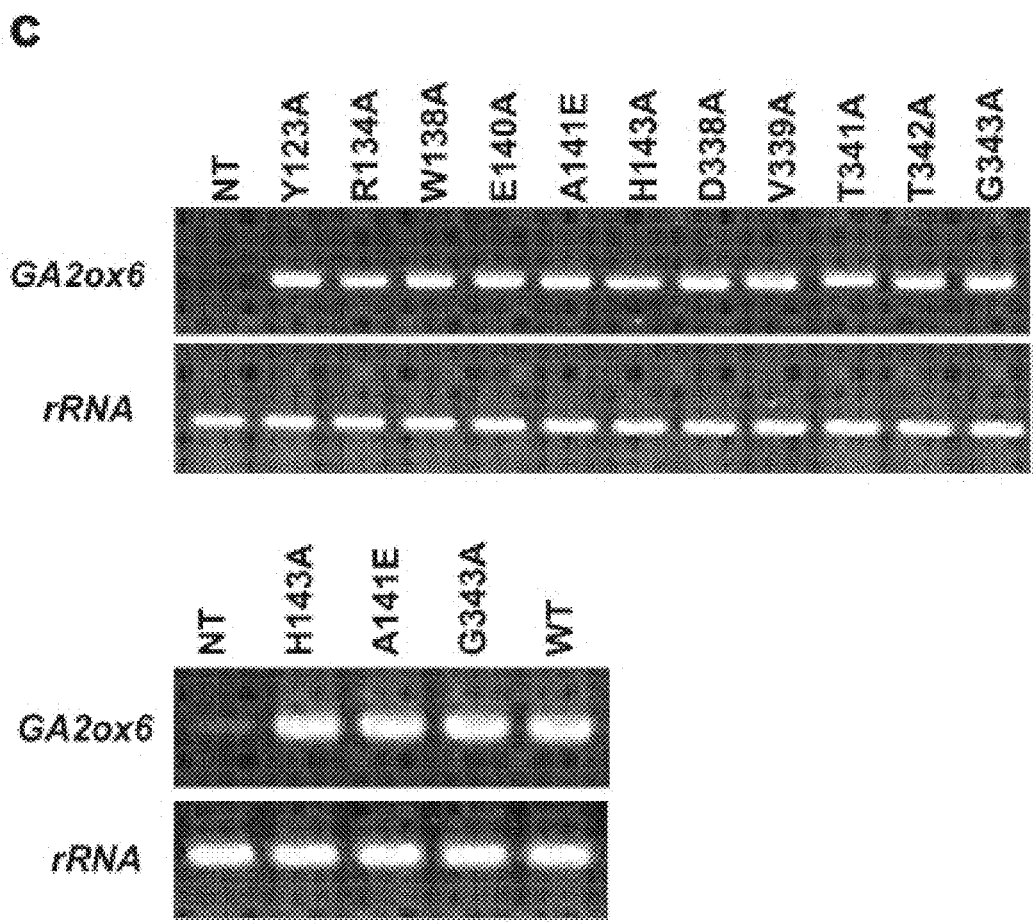
Fig. 2 (Cont')

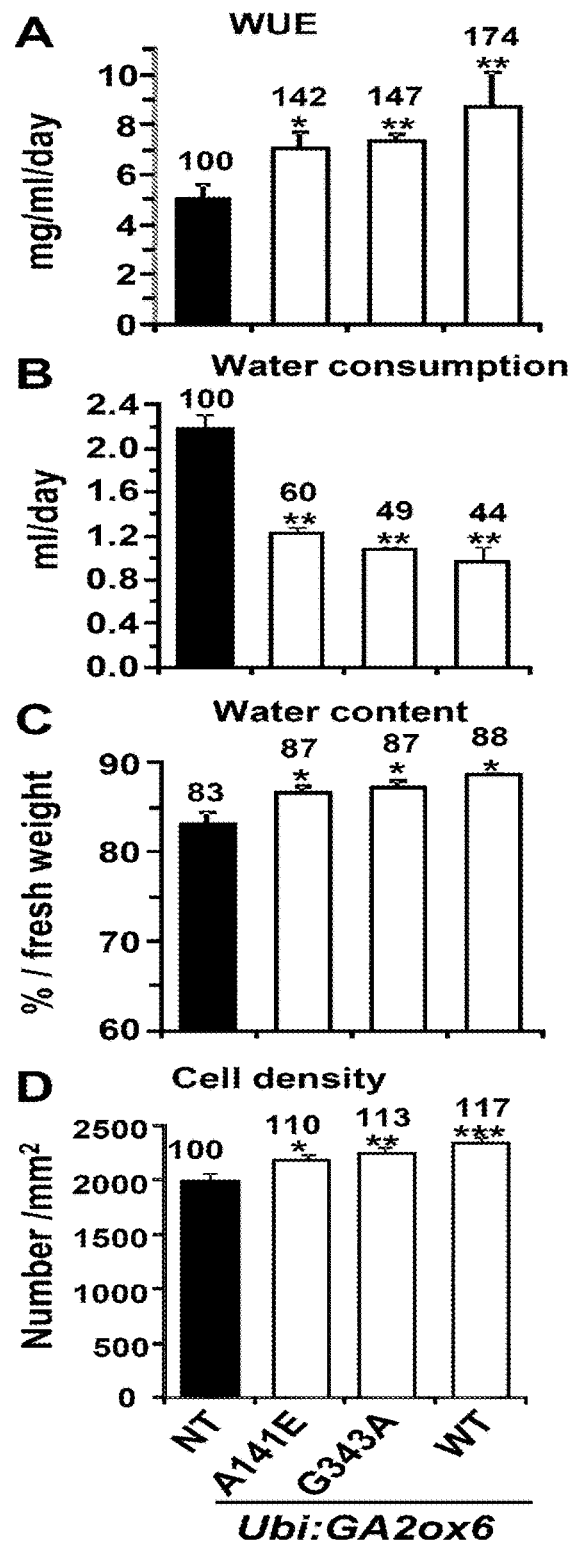
Fig. 9 (Cont')

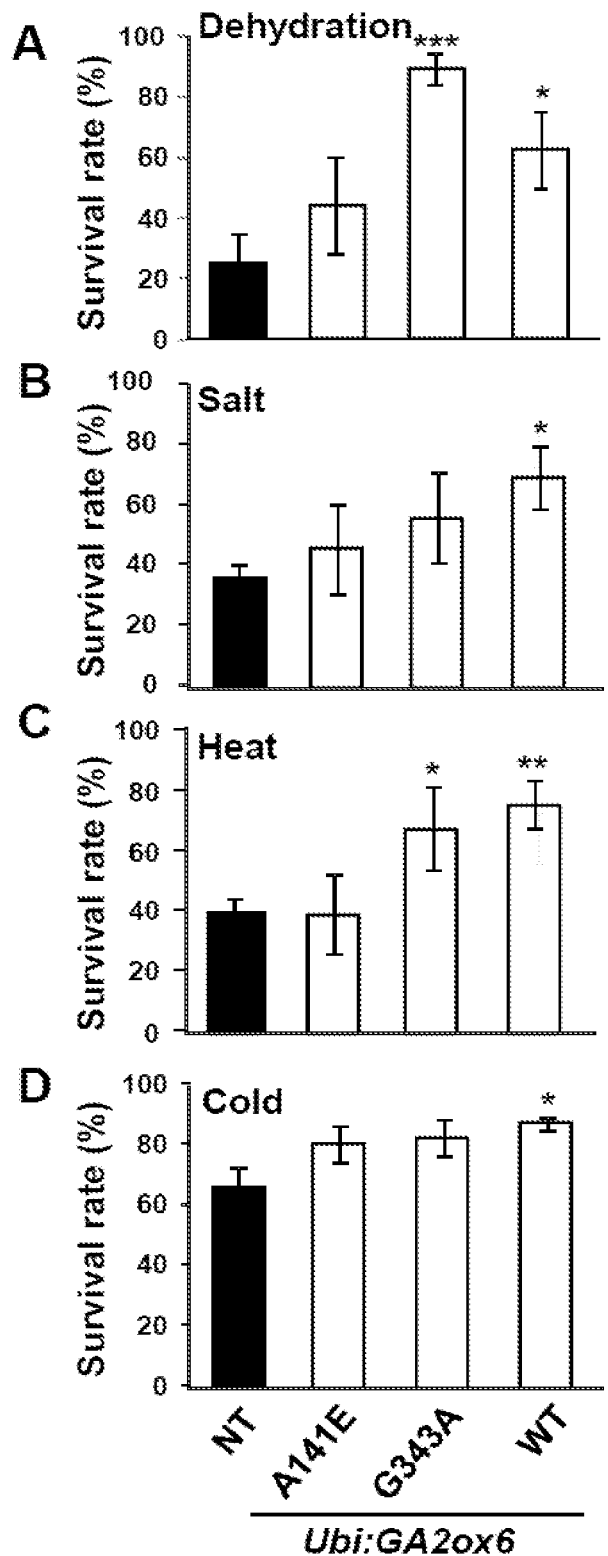
Fig. 10 (Cont')

MUTANT GIBBERELLIN 2-OXIDASE GENES AND USES THEREOF

RELATED APPLICATIONS

This application is a national stage filing under 35 U.S.C. §371 of international PCT application PCT/US2013/072487, filed Nov. 29, 2013, which claims the benefit of U.S. provisional application No. 61/730,737, filed Nov. 28, 2012 under 35 U.S.C. §119, each of which is incorporated by reference herein in its entirety.

TECHNOLOGY FIELD

The present invention relates to mutant gibberellin 2-oxidase (GA2ox) genes and uses thereof.

BACKGROUND OF THE INVENTION

The world's population is projected to rise from the current 7 billion to over 9 billion in the next 40 years, and a parallel increase in global food stocks has become a major challenge in the near future. Rice is a major staple crop feeding more human population than any other crops, and its yield must be increased by at least 40% in order to meet the world's demand for food production. However, the rice yield is close to its upper limit in major rice production countries (IRRI, 2010). Additionally, global climate changes, such as rising temperature and water scarcity, further aggravate the stability of rice production.

The grain yield potential in rice is determined by both genetic and environmental factors (Curtis et al., 2005; Wang and Li, 2005, 2006, 2008; Jeon et al., 2011; Yadav et al., 2011). Examples of regulatory genes identified in rice include LAX (a basic helix-loop-helix transcription factor) which controls shoot and panicle branching (Komatsu et al., 2003), Gn1a (a cytokinin oxidase/dehydrogenase, OsCKX2) which degrades cytokinin in inflorescence meristems and increases grain number (Ashikari et al., 2005), FZP (an ethylene responsive element-binding factor) controls the transformation of floral meristems to inflorescent shoots (Yi et al., 2005), DEP2 (dense and erect panicle 2) (Li et al., 2010) and DEP3 (a patatin-like phospholipase A2 superfamily domain-containing protein) (Qiao et al., 2011) controls panicle morphology, SPL14 (the SQUAMOSA promoter-binding-like protein) controls tiller and panicle developments (Jiao et al., 2010; Miura et al., 2010), and GS5 (a putative serine carboxypeptidase) which controls grain size (Li et al., 2011).

Plant hormones play crucial roles in the regulation of plant architecture and grain yield, and gibberellins (GAs) are a class of essential hormones that control seed germination, plant height, root growth, flowering and seed production (Carrera et al., 2000; Lo et al., 2008; Dayan et al., 2010; Jia et al., 2011). Production and maintenance of optimal levels of bioactive GAs are important for plant normal growth and development. Slight reduction in GA levels results in semi-dwarfism of plant but that are more lodging-resistant and improve the harvest index (the ratio of grain weight to total weight of grains plus straws) (Khush, 1999). Breeding of semi-dwarf wheat and rice cultivars by incorporation of two genes, the Reduced height 1 (Rht1) and semi-dwarf (sd1) that are involved in GA signaling and biosynthesis in wheat and rice, respectively, and with the combination of N-fertilizer application, led to quantum leap of yield increase in the two cereal crops, and that is the basis behind the so called "Green revolution" (Khush, 1999; Peng et al., 1999; Sasaki et al., 2002; Spielmeyer et al., 2002b, a; Botwright et al., 2005b, a).

Recent genetic, biochemical, and structural studies have significantly enhanced our knowledge on biochemical pathways of GA biosynthesis and catabolism, genes and enzymes involved in these pathways and the molecular mechanism of GA signaling in plants (Hartweck, 2008; Sun, 2008; Yamaguchi, 2008; Hedden and Thomas, 2012). GA 3-oxidase (GA3ox) and GA 20-oxidase (GA20ox) are essential enzymes in biosynthesis and GA 2-oxidase (GA2ox) in inactivation of GA metabolites that determines final concentrations of bioactive GA ($GA_1$, $GA_3$, $GA_4$, and $GA_7$) (Hedden and Phillips, 2000).

A major catabolic pathway for GAs is initiated by a 2β-hydroxylation reaction catalyzed by GA2ox. The class $C_{19}$ GA2oxs more commonly found in various plant species hydroxylate the C-2 of active $C_{19}$-GAs ($GA_1$ and $GA_4$) or $C_{19}$-GA precursors ($GA_{20}$ and $GA_9$) to produce biologically inactive GAs (Sakamoto et al., 2004). A class of $C_{20}$ GA2oxs, including Arabidopsis GA2ox7 and GA2ox8, spinach GA2ox3 and rice GA2ox5, GA2ox6, and GA2ox9 that specifically hydroxylate $C_{20}$-GA precursors, are relatively rare and less studied compared with $C_{19}$ GA2oxs (Schomburg et al., 2003; Lee and Zeevaart, 2005; Lo et al., 2008). Class $C_{20}$ GA2oxs contain three unique and conserved amino acid motifs that are absent in class $C_{19}$ GA2oxs (Lee and Zeevaart, 2005; Lo et al., 2008).

Plant architecture, such as plant height, tiller number, and root system, has been important agronomic traits for breeding. Manipulation of GA levels offers an opportunity for further improvement of plant architecture for optimal grain yield potential. GA biosynthesis and catabolism enzymes have been used to control the endogenous level of bioactive GA in transgenic plants. For examples, overexpression of a GA catabolic enzyme, GA2ox1, controlled by a under the control of a GA biosynthesis gene (GA3ox2) promoter results in semi-dwarf transgenic rice with normal in flowering and grain development (Mohanty et al., 2002). Overexpression of a mutated class $C_{19}$ GA2ox6 under the control of ubiquitin promoter produces semi-dwarf transgenic rice with increased tiller number and root system (Abiko et al., 2008). However, constitutive overexpression of GA2oxs normally leads to severe dwarf sterile in transgenic plants (Sakai et al., 2003; Sakamoto et al., 2004). Consequently, different strategies were used to overexpress some of these enzymes. Overexpression of $C_{20}$ GA2oxs seem to offer more beneficial effects on plant growth and architecture, such as bearing more seeds and producing earlier and more tillers and stronger roots and stems as compared with $C_{19}$ GA2oxs (Lo et al., 2008). Deletion of the conserved motif III in $C_{20}$ GA2oxs further improves plant architecture and seed production as compared with the wild type $C_{20}$ GA2oxs in transgenic rice (Lo et al., 2008).

There is a need to fine tune the GA level in plants to retain desired GA deficient advantages, with reduced or no unfavorable defects.

BRIEF SUMMARY OF THE INVENTION

Accordingly, the present invention have conducted studies on whether modification of the three conserved amino acid motifs in $C_{20}$ GA2oxs could be used to fine tune the architecture of transgenic rice.

In the present study, a representative $C_{20}$ GA2oxs, GA2ox6 protein with point mutations in three conserved motifs of rice were generated and overexpressed in transgenic rice. It is unexpectedly found that transgenic rice lines overexpressing certain mutant GA2ox6 (i.e. 123A, 140A, 141E, 143A or 343A) exhibit the desired GA deficient advantages (semi-dwarf, more tillers, thicker stem, more and thicker roots, dark green leaves, and erect plant architecture), with reduced or no unfavorable defects (slow in germination and flowering, low yield).

Therefore, in one aspect, the present invention provides an isolated polynucleotide that encodes a mutant class $C_{20}$ gibberellin 2-oxidase protein ($C_{20}$ GA2ox), wherein the mutant $C_{20}$ GA2ox includes an amino acid mutation selected from the group consisting of:

(i) an amino acid residue corresponding to position 123 of SEQ ID NO: 1 substituted with Alanine (123A), (ii) an amino acid residue corresponding to position 140 of SEQ ID NO: 1 substituted with Alanine (140A), (iii) an amino acid residue corresponding to position 141 of SEQ ID NO: 1 substituted with Glutamate (141E), (iv) an amino acid residue corresponding to position 143 of SEQ ID NO: 1 substituted with Alanine (143A), and (v) an amino acid residue corresponding to position 343 of SEQ ID NO: 1 substituted with Alanine (343A).

In another aspect, the present invention provides an expression vector and a recombinant cell comprising a polynucleotide encoding a mutant $C_{20}$ GA2ox according to the invention.

In still another aspect, the present invention provides a transgenic plant comprising a transgene, wherein the transgene encodes a mutant class $C_{20}$ gibberellin 2-oxidase protein ($C_{20}$ GA2ox), wherein the mutant $C_{20}$ GA2ox includes an amino acid mutation selected from the group consisting of:

(i) an amino acid residue corresponding to position 123 of SEQ ID NO: 1 substituted with Alanine (123A), (ii) an amino acid residue corresponding to position 140 of SEQ ID NO: 1 substituted with Alanine (140A), (iii) an amino acid residue corresponding to position 141 of SEQ ID NO: 1 substituted with Glutamate (141E), (iv) an amino acid residue corresponding to position 143 of SEQ ID NO: 1 substituted with Alanine (143A), and (v) an amino acid residue corresponding to position 343 of SEQ ID NO: 1 substituted with Alanine (343A).

According to the invention, the transgenic plant with the mutant $C_{20}$ GA2ox exhibit one or more moderate GA deficient features, including (i) an increased height or germination rate as compared with a plant transformed with the wild type $C_{20}$ GA2ox, and (ii) shorter in height, higher tiller numbers, earlier tillering, increased root system, lower shoot to root ratio, more efficient water consumption, higher chlorophyll content, higher mesophyll cell density, higher photosynthesis rate, higher grain yield, higher anti-oxidant activity, or higher tolerance to environmental stress, than a non-transgenic plant of the same genetic background while being grown under the same conditions.

The present invention also relates to a method for producing a transgenic plant as described herein, comprising (a) transforming a plant cell with a nucleic acid molecule comprising a transgene encoding a mutant class $C_{20}$ GA2ox as described herein to obtain a recombinant plant cell; and (b) growing the recombinant plant cell obtained in (a) to generate a transgenic plant.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
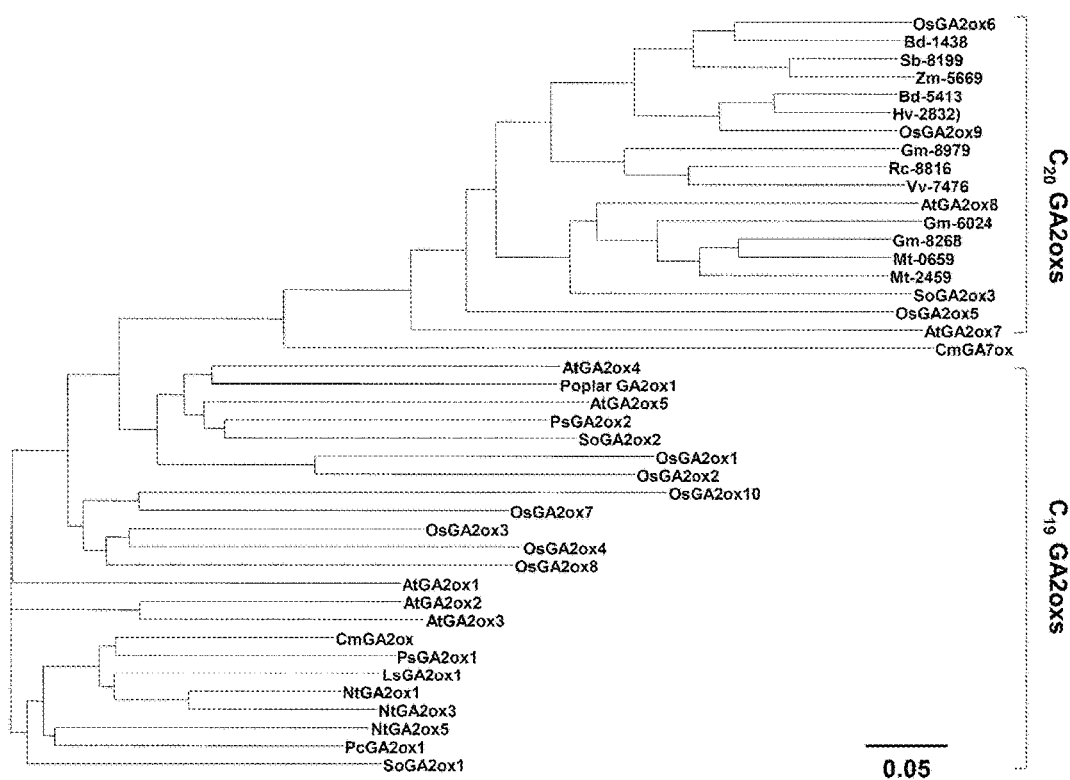
FIG. 1 shows phylogenetic tree based on the comparison of plant GA2oxs. Amino acid sequences of 42 GA2oxs from eleven plant species. C19 and C20 GA2oxs were separated to two clays. The scale value of 0.05 indicates 0.05 amino acid substitutions per site. Plant species: At, *Arabidopsis thaliana*; Bd, *Brachypodium distachyon*; Cm, *Cucurbita maxima*; Gm, *Glycine max*; Hv, *Holdeum vulgare*; Ls, *Lactuca sativa*; Mt, *Medicago truncatula*; Nt, *Nicotiana sylvestris*; Os, *Oryza sativa*; Pc, *Phaseolus coccineus*; PaPt, *Populus alba×P. tremuloides*; Ps, *Pisum sativum*; Rc, *Ricinus communis*; Sb, *Sorghum bicolor*; So, *Spinacia oleracea*; Vv, *Vitis vinifera*; Zm, *Zea mays*.

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant nucleic acid" refers to a polynucleotide or nucleic acid having sequences that are not naturally joined together. A recombinant nucleic acid may be present in the form of a vector. "Vectors" may contain a given nucleotide sequence of interest and a regulatory sequence. Vectors may be used for expressing the given nucleotide sequence (expression vector) or maintaining the given nucleotide sequence for replicating it, manipulating it or transferring it between different locations (e.g., between different organisms). Vectors can be introduced into a suitable host cell for the above mentioned purposes. A "recombinant cell" refers to a cell that has had introduced into it a recombinant nucleic acid.

As used herein, the term "operably linked" may mean that a polynucleotide is linked to an expression control sequence in such a manner to enable expression of the polynucleotide when a proper molecule (such as a transcriptional factor) is bound to the expression control sequence.

As used herein, the term "expression control sequence" or "regulatory sequence" means a DNA sequence that regulates the expression of the operably linked nucleic acid sequence in a certain host cell.

Examples of vectors include, but are not limited to, plasmids, cosmids, phages, YACs or PACs. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., α-mating factor signal) and other control sequence (e.g., Shine-Dalgano sequences and termination sequences). Preferably, vectors may further contain a marker sequence (e.g., an antibiotic resistant marker sequence) for the subsequent screening procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide.

Where the expression vector is constructed for a plant cell, several suitable promoters known in the art may be used, including but not limited to the Figwort mosaic virus 35S promoter, the cauliflower mosaic virus (CaMV) 35S promoter, the *commelina* yellow mottle virus promoter, the rice cytosolic triosephosphate isomerase (TPI) promoter, the rice actin 1 (Act1) gene promoter, the uniquitin (Ubi) promoter, the rice amylase gene promoter, the adenine phosphoribosyltransferase (APRT) promoter of *Arabidopsis*, the mannopine synthase and octopine synthase promoters.

To prepare a transgenic plant, it is preferably that the expression vector as used herein carries one or more selection markers for selection of the transformed plants, for example, genes conferring the resistance to antibiotics such as hygromycin, ampicillin, gentamycine, chloramphenicol, streptomycin, kanamycin, neomycin, geneticin and tetracycline, URA3 gene, genes conferring the resistance to any other toxic compound such as certain metal ions or herbicide, such as glufosinate or bialaphos.

As used herein, the term "transgenic plant" or "transgenic line" refers to a plant that contains a recombinant nucleotide sequence that encodes a gene i.e. a transgene. The transgenic plant can be grown from a recombinant cell.

A variety of procedures that can be used to engineer a stable transgenic plant are available in this art. In one embodiment of the present invention, the transgenic plant is produced by transforming a tissue of a plant, such as a protoplast or leaf-disc of the plant, with a recombinant *Agrobacterium* cell comprising a polynucleotide encoding a desired protein (e.g. a mutant C20 GA2ox) and generating a whole plant from the transformed plant tissue. In another embodiment, a polynucleotide encoding a desired protein can be introduced into a plant via gene gun technology, particularly if transformation with a recombinant *Agrobacterium* cell is not efficient in the plant.

The term "polypeptide" refers to a polymer composed of amino acid residues linked via peptide bonds. The term "protein" typically refers to relatively large polypeptides. The term "peptide" typically refers to relatively short polypeptides.

An "isolated" substance means that it has been altered by the hand of man from the natural state. If an "isolated" substance presents in nature, it has been changed or removed from its original environment, or both. For example, a polypeptide or polynucleotide naturally present in a living subject is not "isolated" but the polypeptide or polynucleotide is isolated if it has been substantially separated from the coexisting materials of its natural state and exist in a substantially pure state.

A variety of procedures that can be used to generate a point mutation such as site-direct mutagenesis that can introduce mutations such as a deletion, insertion or substitution in the site as described herein. See examples below for details.

As used herein, the term "gibberellin 2-oxidase protein" or "GA2ox" refer to an enzyme that initiates a 2β-hydroxylation reaction to inactivate gibberellin (GA) and/or its precursors, thus reducing the endogenous levels of bioactive GAs. "$C_{20}$ GA2ox" is a class $C_{20}$ GA2ox that specifically catalyzes 2β-hydroxylation of $C_{20}$-GA precursors but not $C_{19}$-Gas. $C_{20}$ GA2oxs contain three unique and conserved amino acid motifs that are absent in class $C_{19}$ GA2oxs. The conserved amino acid motifs are motif I: xYRWG (SEQ ID NO: 2), motif II: xxSxSEAxHxxx (SEQ ID NO: 3), and motif III: DVxxxGxKxGLxxF (SEQ ID NO: 4). Examples of $C_{20}$ GA2ox include, but are not limited to, *Arabidopsis* GA2ox7 (SEQ ID NO: 18) and GA2ox8 (SEQ ID NO: 19), spinach GA2ox3 (SEQ ID NO: 20), and rice GA2ox5 (SEQ ID NO: 21), GA2ox6 (SEQ ID NO: 1) and GA2ox9 (SEQ ID NO: 22). In one certain embodiment, the $C_{20}$ GA2ox as used herein is GA2ox6 (SEQ ID NO: 1), the corresponding cDNA sequence being SEQ ID NO: 65.

The amino acid sequence of the polypeptide described herein may include its biological equivalent, which means that there is a limited number of changes or modifications that may be made within a certain portion of the molecule irrelevant to the activity or function of the protein (such as regions other than the motifs I, II and III of $C_{20}$ GA2ox) and still result in a molecule with an substantially the same level of the biological activity. Biologically equivalent polypeptides are thus defined herein as those polypeptides in which certain amino acid residues may be substituted. Polypeptides with different substitutions may be made and used in accordance with the invention. Modifications and changes may be made in the structure of such polypeptides and still obtain a molecule having similar or desirable characteristics. For example, certain amino acids may be substituted for other amino acids in the peptide/polypeptide structure without appreciable loss of activity. Amino acid substitutions are generally based on the relative similarity of the amino acid side-chain substituents, for example, their hydrophobicity, hydrophilicity, charge, size, and the like. For example, arginine (Arg), lysine (Lys), and histidine (His) are all positively charged residues; and alanine (Ala), glycine (Gly) and serine (Ser) are all in a similar size. Therefore, based upon these considerations, arginine (Arg), lysine (Lys) and histidine (His); and alanine (Ala), glycine (Gly) and serine (Ser) may be defined as biologically functional equivalents. One can readily design and prepare recombinant genes for microbial expression of polypeptides having equivalent amino acid residues.

For example, particular examples of $C_{20}$ GA2ox, as described herein, Arabidopsis GA2ox7 (SEQ ID NO: 18) and GA2ox8 (SEQ ID NO: 19), spinach GA2ox3 (SEQ ID NO: 20), and rice GA2ox5 (SEQ ID NO: 21), GA2ox6 (SEQ ID NO: 1) and GA2ox9 (SEQ ID NO: 22) includes its biological equivalent, having at least 50%, 60%, or 65%, or 70%, or 75%, or 80%, or 85%, or 90%, or 95% identity to its respective sequence and possess the conserved structure, i.e. motif I: xYRWG (SEQ ID NO: 2), motif II: xxSxSE-AxHxxx (SEQ ID NO: 3), and motif III: DVxxxGxKxGLxxF (SEQ ID NO: 4). In one certain example, GA2ox6 (SEQ ID NO: 1) includes motif I (SEQ ID NO: 5), motif II (SEQ ID NO: 6), and motif I (SEQ ID NO: 7).

To determine the percent identity of two amino acid sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

The enzymatic activity of $C_{20}$ GA2ox with or without mutation can be analyzed using various methods known in the art, such as those described in U.S. patent application Ser. No. 12/139,674 (U.S. Pat. No. 8,034,992) the entire content of which is incorporated herein by reference. For example, $C_{20}$ GA2ox can be purified from a plant or a recombinant cell that expresses the $C_{20}$ GA2ox and then the enzyme activity to hydroxylate a class $C_{20}$-GA precursor can be assayed by using a radio-labeled $C_{20}$-GA precursor (see Lee and Zeevaart, 2002; Schomburg et al., 2003). An in vivo assay can also be used to measure the enzyme activity of C20 GA2ox, such as by analyzing the amount of $GA_1$ or $GA_{97}$ in plant extracts (from leaves or seedlings). In addition, since overexpression of $C_{20}$ GA2ox results in decreased plant height that is easy to be observed, one can also use plant height to determine the relative impact of mutation of $C_{20}$ GA2ox enzyme activity in transgenic plant.

As used herein, the term "moderate GA level" can mean a moderate (mediate) level of GA amount in plants, i.e. between a normal endogenous GA level in a natural non-transgenic (NT) plant and that in a transgenic plant overexpressing a wild type C20 GA2ox which inactivates biologically active GA or its precursors, thus reducing the endogenous level of biological GAs. According to the invention, a moderate GA level leads to one or more moderate GA deficient features, including (i) an increased height or germination rate as compared with a plant overexpressed with a wild type class C20 GA2ox, and (ii) shorter in height, higher tiller numbers, earlier tillering, increased root system, lower shoot to root ratio, more efficient water consumption, higher chlorophyll content, higher mesophyll cell density, higher photosynthesis rate, higher grain yield, higher anti-oxidant activity, or higher tolerance to environmental stress, than a non-transgenic plant of the same genetic background while being grown under the same conditions.

In our previous study, the GA2ox genes, including C20 GA2oxs, were identified and disclosed in U.S. patent application Ser. No. 12/139,674 (U.S. Pat. No. 8,034,992) the entire content of which is incorporated herein by reference.

In the present study, five effective mutations (i.e. 123A, 140A, 141E, 143A or 343A) are disclosed which can reduce C20 GA2oxs enzymatic activity to different extents, leading to various degrees of GA deficient yet beneficial agronomic traits as above described.

Therefore, in one aspect, the present invention provides an isolated polynucleotide that encodes a mutant class C20 gibberellin 2-oxidase protein (C20 GA2ox), wherein the mutant GA2ox includes an amino acid mutation selected from the group consisting of:

(i) an amino acid residue corresponding to position 123 of SEQ ID NO: 1 substituted with Alanine (123A), (ii) an amino acid residue corresponding to position 140 of SEQ ID NO: 1 substituted with Alanine (140A), (iii) an amino acid residue corresponding to position 141 of SEQ ID NO: 1 substituted with Glutamate (141E), (iv) an amino acid residue corresponding to position 143 of SEQ ID NO: 1 substituted with Alanine (143A), and (v) an amino acid residue corresponding to position 343 of SEQ ID NO: 1 substituted with Alanine (343A).

In certain embodiments, the C20 GA2ox is Arabidopsis GA2ox7 (SEQ ID NO: 18) or GA2ox8 (SEQ ID NO: 19), spinach GA2ox3 (SEQ ID NO: 20), or rice GA2ox5 (SEQ ID NO: 21), GA2ox6 (SEQ ID NO: 1) or GA2ox9 (SEQ ID NO: 22).

In one particular example, the C20 GA2ox is GA2ox6 (SEQ ID NO: 1).

In some embodiment, the mutant C20 GA2ox protein comprises an amino acid sequence selected from the group consisting of SEQ ID NO: 8, SEQ ID NO: 9, SEQ ID NO: 10, SEQ ID NO: 11, and SEQ ID NO: 12.

In some embodiment, the isolated polynucleotide encoding the mutant C20 GA2ox protein is selected from the group consisting of SEQ ID NO: 13, SEQ ID NO: 14, SEQ ID NO: 15, SEQ ID NO: 16, and SEQ ID NO: 17.

The polynucleotide according to the present invention can be inserted into a suitable expression vector to transform plant cells.

Accordingly, the present invention provides a recombinant vector comprising the polynucleotide as described herein. The polynucleotide sequence according to the invention can be operably linked to an expression control sequence, and the polynucleotide sequence operably linked to the expression control sequence can form an expression cassette which can be included in an expression vector containing other elements such as a selection marker and a replication origin. The expression control sequence includes a promoter for initiating transcription; an optional operator sequence for controlling transcription, a sequence relating a suitable mRNA ribosome-binding site, and a sequence for termination. Vectors suitable to introduce the inventive polynucleotide into plant cells include a Ti plasmid, a root-inducing (Ri) plasmid and a plant virus vector. Examples of the suitable vectors include, but are not limited to, binary vectors, such as pGA, pPZP and pCAMBIA series. Persons skilled in the art can choose a vector suitable to introduce the polynucleotide of the invention into a plant.

The introduction of said recombinant vector into cells can be performed using any method known in the art. Thus, the present invention provides a recombinant cell transformed with the expression vector of the invention. In one embodiment, the recombinant cell can be a plant cell or a *Agrobacterium* cell.

The present invention also provides an isolated polypeptide encoded by the polynucleotide that encodes a mutant $C_{20}$ GA2ox as described herein. The polypeptide of the invention can be prepared by culturing a recombinant cell transformed with the expression vector of the invention in a suitable condition and conducting purification by methods known in the art.

The present invention also provides a transgenic plant comprising a transgene, wherein the transgene encodes a mutant C20 GA2ox as described herein, which is selected from the group consisting of: (i) an amino acid residue corresponding to position 123 of SEQ ID NO: 1 substituted with Alanine (123A); (ii) an amino acid residue corresponding to position 140 of SEQ ID NO: 1 substituted with Alanine (140A); (iii) an amino acid residue corresponding to position 141 of SEQ ID NO: 1 substituted with Glutamate (141E); (iv) an amino acid residue corresponding to position 143 of SEQ ID NO: 1 substituted with Alanine (143A); and (v) an amino acid residue corresponding to position 343 of SEQ ID NO: 1 substituted with Alanine (343A).

Plants to which the inventive method can be applied include both monocotyledon and dicotyledon. Examples of monocotyledon includes but not limited to rice, barley, wheat, rye, oat, corn, bamboo, sugar cane, onion, leek and ginger. Examples of the dicotyledons include, but are not limited to *Arabidopsis thaliana*, eggplant, tobacco plant, red pepper, tomato, burdock, crown daisy, lettuce, balloon flower, spinach, chard, sweet potato, celery, carrot, water dropwort, parsley, Chinese cabbage, cabbage, radish, watermelon, melon, cucumber, pumpkin, gourd, strawberry, soybean, mung bean, kidney bean, and pea. In one particular embodiment of the present invention, the transgenic plant is a transgenic cereal plant, preferably a transgenic rice plant.

According to the invention, a plant overexpressed with a mutant C20 GA2ox gene exhibits various degrees of GA deficient yet beneficial agronomic traits, including (i) an increased height or germination rate as compared with a plant transformed with a wild type class C20 GA2ox, and (ii) shorter in height, higher tiller numbers, earlier tillering, increased root system, lower shoot to root ratio, more efficient water consumption, higher chlorophyll content, higher mesophyll cell density, higher photosynthesis rate, higher grain yield, higher anti-oxidant activity, or higher tolerance to environmental stress, than a non-transgenic plant of the same genetic background while being grown under the same conditions. In one certain embodiment, the transgenic plant of the invention has a height that is about 25% to 99%, 30% to 70%, or 40% to 60% of a non-transgenic plant.

Thus, the present invention also provides a method for producing a transgenic plant, comprising (a) transforming a plant cell with a nucleic acid molecule comprising a transgene encoding a mutant C20 GA2ox as described herein to obtain a recombinant plant cell; and (b) growing the recombinant plant cell obtained in (a) to generate a transgenic plant.

To select a pant with desired traits, the method of the invention further comprises (c) selecting a transgenic plant which is higher in height, or has a higher germination rate as compared with a plant of the same genetic background transformed with the wild type class C20 GA2ox while being grown under the same conditions.

In another embodiment, the method of the invention further comprises (c) selecting a transgenic plant which is shorter such as having a height that is about 25% to 99%, 30% to 70%, or 40% to 60% of a non-transgenic plant of the same genetic background while being grown under the same conditions.

In still another embodiment, the method of the invention further comprises (c) selecting a transgenic plant exhibiting higher tiller numbers, earlier tillering, increased root system, lower shoot to root ratio, more efficient water consumption, higher chlorophyll content, higher mesophyll cell density, higher photosynthesis rate, higher grain yield, higher anti-oxidant activity, or higher tolerance to environmental stress, than a non-transgenic plant of the same genetic background while being grown under the same conditions. Examples of the environmental stress include but are not limited to drought, temperature, salinity and oxidative stresses.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

1. MATERIALS AND METHODS

1.1 Plant Materials

The rice cultivar *Oryza sativa* L. cv Tainung 67 was used in this study. GA deficient transgenic and NT seeds were surface sterilized in 2.5% NaClO and placed on MS agar medium (Murashige and Skoog Basal Medium, Sigma), and incubated at 28° C. with 16 h light and 8 h dark for 15~20 days. Plants were transplanted to pot soil and grown in a net-house.

1.2 Site-Directed Mutation of Rice GA2ox6 and Rice Transformation

For generation of point-mutated GA2ox6 in three conserved domains, amino acid residues Y123, R134, W138, E140, H143, D338, V339, T342, G343 were substituted by alanine, and A141 was substituted by glutamate. Point mutations were performed as described (Kunkel, 1985). Ubi:GA2ox6 in plasmid pAHC18 (Lo et al., 2008) was as the template for point mutation of Ubi: GA2ox6 by Quick-Change® site-directed mutagenesis kit (Stratagene, www.stratagene.com/) according to the manufacturer's instructions. Primers for mutagenesis are listed in supplemental Table 5, and mutated sequences were confirmed by genomic DNA sequencing of transgenic plants. All plasmids were linearized with HindIII and inserted into the same site in pCAMBIA1301 (Hajdukiewicz et al., 1994). Resulting binary vectors were transferred into *Agrobacterium tumefaciens* strain EHA105 and used for rice transformation as described (Krugel et al., 2002).

1.3 Stress Treatments

Fourteen-day-old seedlings were transplanted to distilled water for one day, and then incubated in cold (4° C.) or heat (42° C.) chamber or in 200 mM NaCl solution for 2 days, or dehydration on bench at room temperature (25-27° C.) for 6 hours. All stressed plants were recovered in water for 6 days at 28° C. incubator, and survival rates were determined.

1.4 Leaf Structure Examination

The first fully expanded leaf of 18-day-old seedling was collected. Cross sections of leaf blades were made with Microslicers DTK-1000 (TED PELLA, Inc.) and examined with a light microscope (Axiolmager Z1, Carl Zeiss Inc.). The first fully expanded leaf of 80 day-old adult (before heading stage) plants were cut from the one third part from the tip, and stained with fast green and observed under microscope with 100 fold of magnification for quantification of cell density.

1.5 Determination of Water Consumption

Eighteen-day-old seedlings were weighted, then transferred into 50 ml plastic tubes containing 50 ml $H_2O$, and tube openings were sealed with parafilm. Water consumptions were recorded once every 2 days with a total of 8 days. The fresh weight increasement of total plants and final fresh and dry weights were determined.

1.6 Quantification of Total Chlorophyll, Chlorophyll a and b Content and Maximum Photosynthetic Rate Assay Fresh leaves were collected from the first expanded leaf of 80 day-old plants in field. These leaves were then ground with liquid nitrogen in a mortar with pestle. Pigments were extracted with 95% ethanol, and light absorption at 648.6 and 664.2 nm were determined using a UV/Visible spectrophotometer. Concentrations of total chlorophylls, chlorophyll a and b were calculated as described (Lichtenthaler 1987).

Leaf photosynthetic rate was detected by using the LI-6400 portable photosynthesis System attached with Leaf Chamber Fluorometer (Model 6400-40, LICOR Inc.)

1.7 Quantification of Proline and Total Peroxides Contents

Shoots of fifteen-day-old seedlings with or without 3 hours of dehydration treatment were weighted and extracted for the quantification of proline and total peroxides; Proline quantification was performed by ninhydrin reagent, the absorbance at 520 nm was calculated by a calibration curve and expressed as µmol proline g-1 fresh weight (Bates et al., 1973). Shoots of fifteen-day-old seedlings were extracted by 5% (w/v) trichloroacetic acid (TAC) for total peroxides content analysis according to the method described by Sagisaka (Sagisaka, 1976).

1.8 Activity Assay of Antioxidant Enzymes

Shoots of fifteen-day-old seedlings with or without 3 hours of dehydration treatment, were extracted using sodium phosphate buffer (50 mM, pH6.8) for the antioxidant enzyme activity assay of catalase and ascorbate peroxidase by spectrophotometric methods. Catalase was assayed according to the method described by Kato and Shimizu (Kato and Shimizu, 1985). Ascorbate peroxidase was performed by the method by Nakano and Asada (Nakano and Asada, 1981).

1.9 Statistical Analysis

All numerical data are presented as mean±SEM (Error bars indicate standard error of the mean). Statistically analyses were carried out with Student's t-test using the Sigma-Plot software (version 11.0, Systat Software, Inc.).

1.10 RT-PCR and Semi-Quantitative RT-PCR Analyses

Total RNA was purified from rice leaves, and RT-PCR and quantitative RT-PCR analyses were conducted as described (Lo et al., 2008).

1.11 Database Searching and Phylogenetic Analysis of $C_{20}$ GA2oxs

Database search for GA2oxs from different plant species and identification of $C_{20}$ GA2oxs using the 30 amino acids present in three unique conserved motifs in rice GA2ox6 were carried out as described (Lo et al., 2008). Deduced amino acid sequences of all $C_{19}$ and $C_{20}$ GA2oxs were aligned as described (Lo et al., 2008).

1.12 Primers

Nucleotides for all primers used for PCR and RT-PCR analyses are provided in Table 1.

TABLE 1

Primers used for T-DNA flanking sequence, PCR and RT-PCR analyses and plasmid constructions.

| Primers | Sequence | Gene |
|---|---|---|
| Primers for site-directed mutagenesis | | |
| Y123A-F (SEQ ID NO: 23) | 5'-CTCAACGGCTCGGCTCGGTGGGGCAAC-3' | |
| Y123A-R (SEQ ID NO: 24) | 5'-GTTGCCCCACCGAGCCGAGCCGTTGAG-3' | |
| R134A-F (SEQ ID NO: 25) | 5'-CGTCGCTCGCTCACCTCTCGTGGTC-3' | |
| R134A-R (SEQ ID NO: 26) | 5'-GACCACGAGAGGTGAGCGAGCGACG-3' | |
| W138A-F (SEQ ID NO: 27) | 5'-CCACCTCTCGGCTTCGGAGGCGTTC-3' | |
| W138A-R (SEQ ID NO: 28) | 5'-GAACGCCTCCGAAGCCGAGAGGTGG-3' | |
| E140A-F (SEQ ID NO: 29) | 5'-CTCTCGTGGTCGGCTGCGTTCCACGTC-3' | |
| E140A-R (SEQ ID NO: 30) | 5'-GACGTGGAACGCAGCCGACCACGAGAG-3' | |
| A141E-F (SEQ ID NO: 31) | 5'-CGTGGTCGGAGGAGTTCCACGTCCC-3' | |
| A141E-R (SEQ ID NO: 32) | 5'-GGGACGTGGAACTCCTCCGACCACG-3' | |
| H143A-F (SEQ ID NO: 33) | 5'-GTCGGAGGCGTTCGCCGTCCCGCTCG-3' | |
| H143A-R (SEQ ID NO: 34) | 5'-CGAGCGGGACGGCGAACGCCTCCGAC-3' | |
| D338A-F (SEQ ID NO: 35) | 5'-GAAGGTGCAGGAAGCCGTCAGGACAAC-3' | |
| D338A-R (SEQ ID NO: 36) | 5'-GTTGTCCTGACGGCTTCCTGCACCTTC-3' | |
| V339A-F (SEQ ID NO: 37) | 5'-GTGCAGGAAGACGCCAGGACAACCG-3' | |
| V339A-R (SEQ ID NO: 38) | 5'-CGGTTGTCCTGGCGTCTTCCTGCAC-3' | |
| T341A-F (SEQ ID NO: 39) | 5'-GAAGACGTCAGGGCAACCGGGAAAAAG-3' | |
| T341A-R (SEQ ID NO: 40) | 5'-CTTTTTCCCGGTTGCCCTGACGTCTTC-3' | |
| T342A-F (SEQ ID NO: 41) | 5'-GAAGACGTCAGGACAGCCGGGAAAAAG-3' | |
| T342A-R (SEQ ID NO: 42) | 5'-CTTTTTCCCGGCTGTCCTGACGTCTTC-3' | |
| G343A-F (SEQ ID NO: 43) | 5'-CAGGACAACCGCCAAAAAGATTGGCCTC-3' | |
| G343A-R (SEQ ID NO: 44) | 5'-GAGGCCAATCTTTTTGGCGGTTGTCCTG-3' | |
| RT-PCR-analysis of gene expression | | |
| GA2ox1-F (SEQ ID NO: 45) | 5'-CGAGCAAACGATGTGGAAGGGCTACAGG-3' | OsGA2ox1 (332 bp) |
| GA2ox1-R (SEQ ID NO: 46) | 5'-TGGCTCAGGCGGAGTGAGTACATTGTCG-3' | |
| GA2ox2-F (SEQ ID NO: 47) | 5'-CCCCACATCCCTGACAAGGCTC-3' | OsGA2ox2 (592 bp) |
| GA2ox2-R (SEQ ID NO: 48) | 5'-CTATTCATGGTCGTCATCGTCC-3' | |
| GA2ox3-F (SEQ ID NO: 49) | 5'-TGAGCGCGCTGGTGACGGCGGA-3' | OsGA2ox3 (451 bp) |
| GA2ox3-R (SEQ ID NO: 50) | 5'-CTTGATTTGTAGGCAGCCTTC-3'- | |

TABLE 1 -continued

Primers used for T-DNA flanking sequence, PCR and RT-PCR analyses and plasmid constructions.

| Primers | Sequence | Gene |
|---|---|---|
| GA2ox5-F (SEQ ID NO: 51) | 5'-ATGGAGGAGCACGACTACGACT-3' | OsGA2ox5 (974 bp) |
| GA2ox5-R (SEQ ID NO: 52) | 5' TCCTCCATGATCTGCTTCCTGTA-3' | |
| GA2ox6-F (SEQ ID NO: 53) | 5'-GACGACGTGCTTCCTGCGGCTCAA-3' | OsGA2ox6 (389 bp) |
| GA2ox6-R (SEQ ID NO: 54) | 5'-CTTCCTGCACCTTCTTCCTGTA-3' | |
| GA2ox9-F (SEQ ID NO: 55) | 5'-ATGTCGAGGCTGGCCAGGG-3' | OsGA2ox9 (533 bp) |
| GA2ox9-R (SEQ ID NO: 56) | 5'-CATACGAGGAAATTACTGAGGC-3' | |
| GA3ox2-F (SEQ ID NO: 57) | 5'-TCTCCAAGCTCATGTGGTCCGAGGGCTA-3' | OsGA3ox2 (346 bp) |
| GA3ox2-R (SEQ ID NO: 58) | 5'-TGGAGCACGAAGGTGAAGAAGCCCGAGT-3' | |
| AMY3-F (SEQ ID NO: 59) | 5'-GCACGGCAAGGACTACAGCG-3' | AMY3 (237 bp) |
| AMY3-R (SEQ ID NO: 60) | 5'-CCTGCCTACTTATTCGAACG-3' | |
| LEA3-F (SEQ ID NO: 61) | 5'-AGCAAGGACAAGGCGAGCGAG-3' | LEA3 (292 bp) |
| LEA3-R (SEQ ID NO: 62) | 5'-CGGCGGTCTTCTGCTTGGCG-3' | |
| 18S-F (SEQ ID NO: 63) | 5'-CCTCGTGCCCCTATCAACTT-3' | 18S rRNA (201 bp) |
| 18S-R (SEQ ID NO: 64) | 5'-GACACTAAAGCGCCCGGTAT-3' | |

2. RESULTS

2.1 Essential Amino Acids in Three Conserved Motifs for Functions of $C_{20}$ GA2oxs in Rice A total of 42 putative GA2oxs were identified by BLAST search of NCBI, TIGR and RiceGAAS databases, and phylogenetic analyses divided class $C_{20}$ and $C_{19}$ GA2oxs into two distinct clays (FIG. 1). By using 30 amino acids reside within three unique conserved motifs of rice GA2ox6 (Lee and Zeevart, 2005; Lo et al., 2008) to blast against the NCBI database, 18 putative $C_{20}$ GA2oxs genes were identified from 8 different plant species (FIG. 2A). All $C_{20}$ GA2oxs contain three conserved motifs, and a total of 16 out of 30 amino acids in these motifs were identical among all $C_{20}$ GA2oxs, including motif I: xYRWG (SEQ ID NO: 2), motif II: xxSxSEAxHxxx (SEQ ID NO: 3), and motif III: DVxxxGxKxGLxxF (SEQ ID NO: 4) (FIG. 2A).

To identify essential amino acid residues in three conserved motifs for biological function, the function prediction was performed by structure prediction; GA2ox6 with point mutations in these motifs were generated and overexpressed under the control of the Ubi promoter in transgenic rice. A total of 11 amino acids were substituted with Alanine (A) except residue Alanine 141 was replaced with Glutamate (E) (FIG. 2A). Correct point mutations in recombinant GA2ox6 were confirmed by genomic DNA sequencing of transgenic rice, and RT-PCR analyses showed that individual GA2ox6 mutants were expressed at similar levels in independent transgenic plants (FIG. 2C). The relative plant height was then used to score the relative impact of mutation in transgenic rice. Mutants Y123A (motif I) and H143A (motif II) abolished and maintained 9% enzyme function, respectively; mutants E140A and A141E (motif II) and G343A (motif III) maintained 42, 55 and 66% enzyme functions, respectively; and the rest mutants of unique amino acids among conserved motifs maintained 80 and 82% enzyme functions (D338A, V339A; motif III); and the other two mutants for highly conserved amino acids, W138 A and T341Astill maintained more than 100% of enzyme functions (FIG. 2B).

Five transgenic lines Y123A, E140A, A141E, H143A and G343A exhibiting increased plant heights as compared with transgenic line overexpressing the wild type GA2ox6 (GA2ox6-WT) were further characterized. Delay in germination rate (FIG. 3) was almost completely recovered to the level of non-transformant (NT). Plant height was significantly reduced (FIG. 4A) and tillering was initiated earlier (FIG. 4B) in seedlings of lines A141E, G343A and GA2ox6-WT than in NT and lines Y123A, H143A and E140A. Flowering time in all transgenic lines except GA2ox6-WT was similar to NT (FIG. 5). The relative heights of adult plants were similar to seedlings (FIG. 4A).

Figure 4:
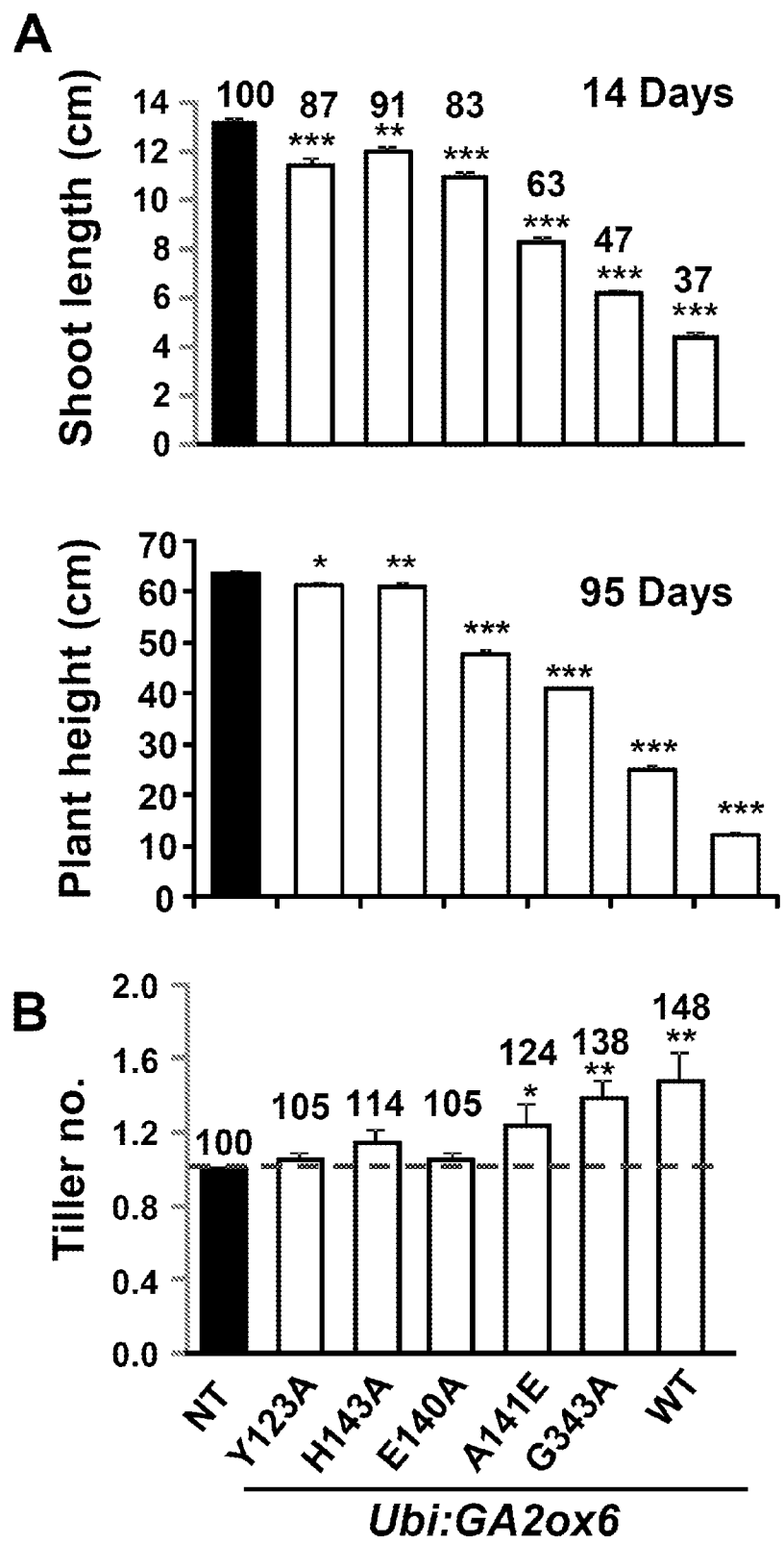
FIG. 4 shows different degrees of developmental responses to GA deficiency in transgenic rice overexpressing point-mutated GA2ox6. 14-day-old and 95-day-old transgenic rice plants overexpressing Y123, E140, A141, H143, and G343 GA2ox6 were used for determination of following parameters. (A) Y123A, E140A, A141E, H143A, and G343A transgenic plants exhibited different degrees of GA deficiency in seedlings (14 DAI, scale bar=2 cm) (upper panel) and mature plants (95 DAI, scale bar=10 cm) (lower panel). (B) Tiller number.
Figure 5:
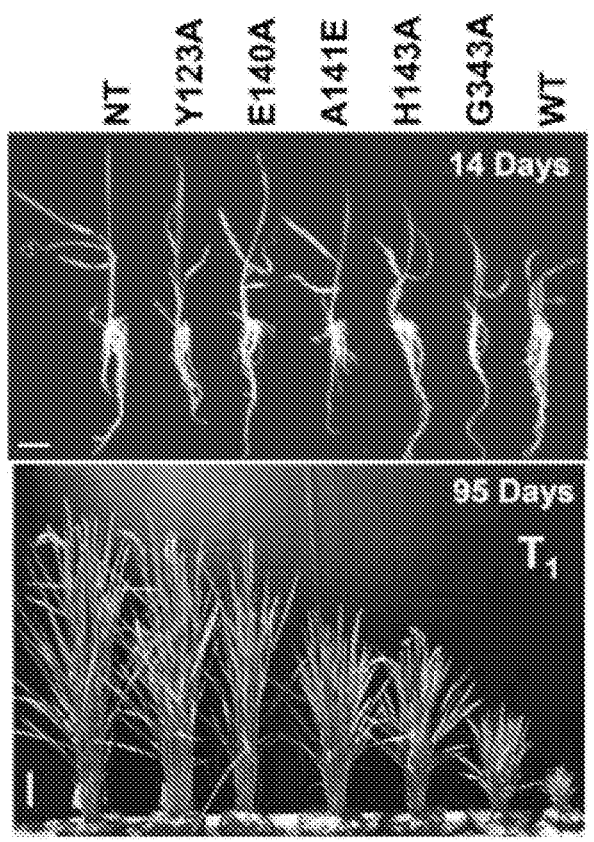
FIG. 5 shows that Y123A, E140A, A141E, H143A, and G343A transgenic plants exhibited different levels of GA deficiency from seedlings to mature plants (14 DAI, scale bar=2 cm; 95 DAI, scale bar=10 cm).
Figure 6:
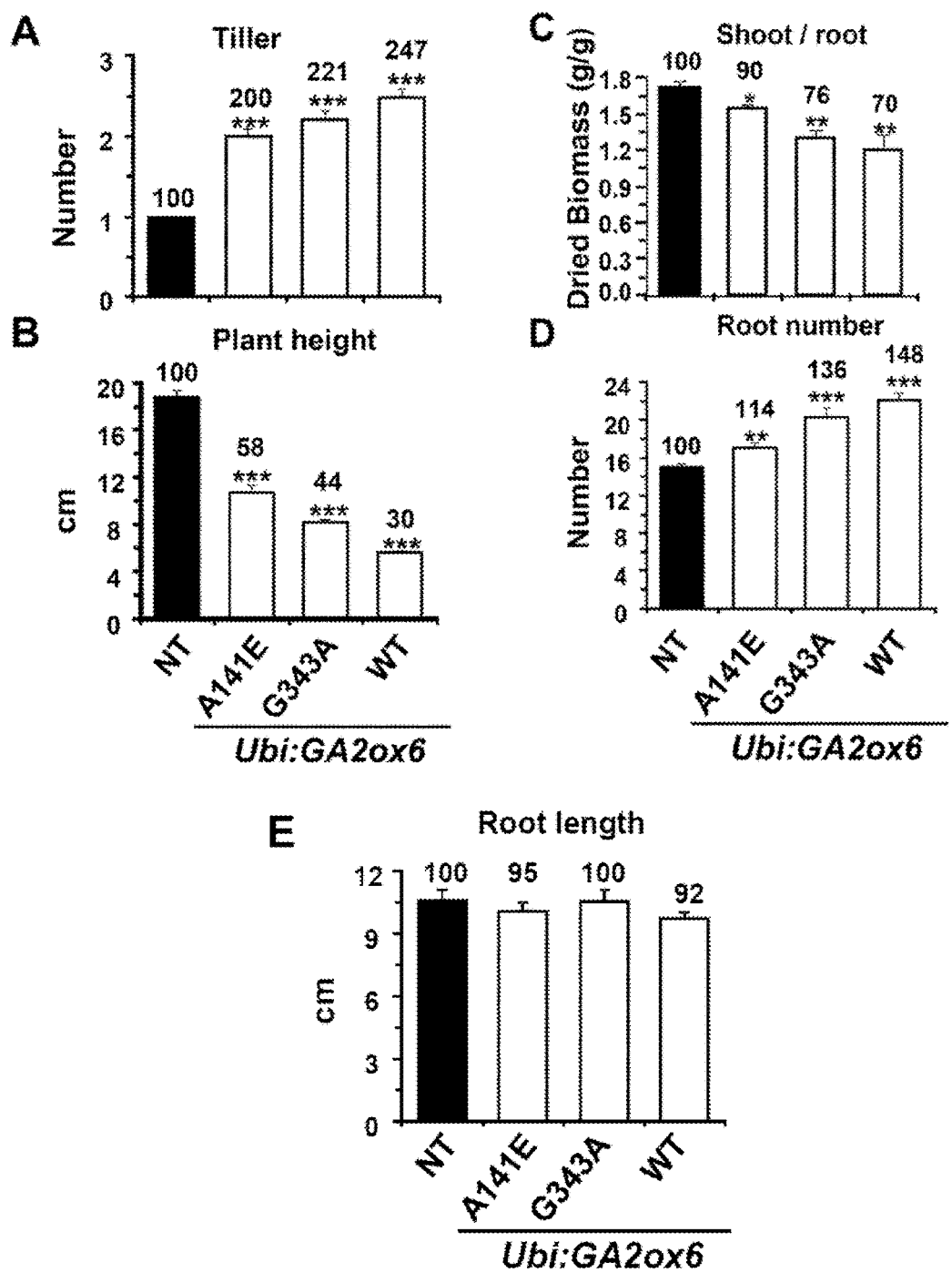
FIG. 6 GA deficient transgenic rice overexpressing A141E and G343A GA2ox6 exhibits increased tiller number, root number and decreased shoot to root ratio. (A) Tiller number were counted at 14 DAI. (B) Plant height were measured at 14 DAI. (C) Shoot to root ratio were estimated at 26 DAI. (D) Root number were counted at 14 DAI. (E) Root length were measured at 14 DAI. Error bars indicate standard error of the mean, SEM. n=16 for each line. Difference was compared between transgenic lines and WT. Significance levels: * P<0.05,  P<0.01, * P<0.001.
Figure 7:
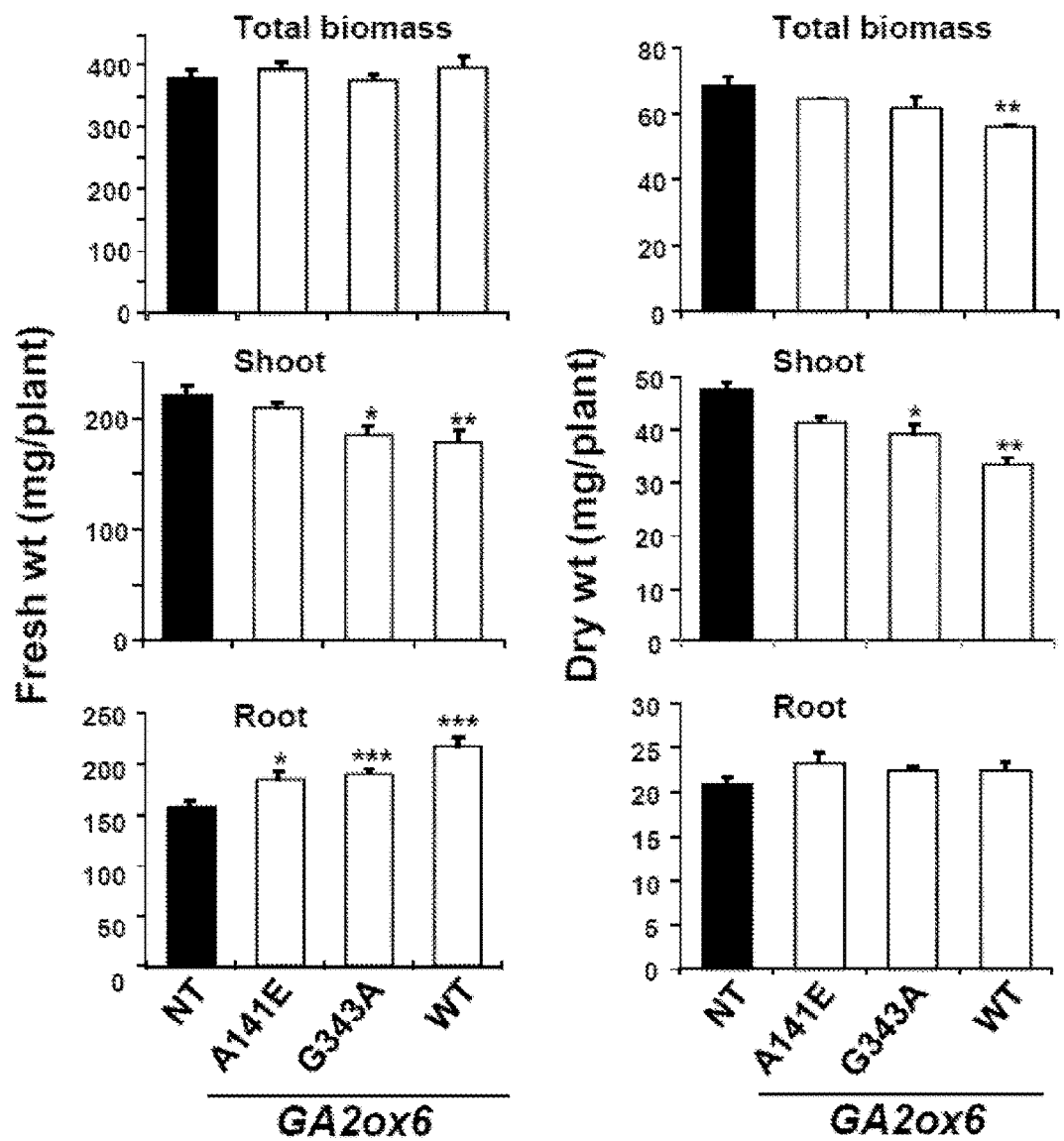
FIG. 7 shows that GA deficient transgenic rice overexpressing GA2ox6 mutants have less shoot biomass but stronger root system. Transgenic plants overexpressing A141E and G343A GA2ox6 had similar total biomass (upper panels), less shoot weight (middle panels) but higher root biomass (lower panels). Value were determined with 20-day-old seedlings. n=21 for each line Error bars indicate standard error of the mean, SEM. Difference was compared between transgenic lines and WT. Significance levels: * P<0.05,  P<0.01, * P<0.001.

2.2 Morphology of GA Deficient Transgenic Rice Overexpressing A141E and G343A GA2ox6 Possess More Potential Morphology for Crop Improvement Preliminary field evaluation indicated that among five transgenic lines, the grain yield of lines A141E and G343A was close to or even higher than NT, and were therefore selected for further characterization for various agronomic traits in seedlings and adult plants grown in field conditions (FIG. 6, FIG. 7, FIG. 4). Tiller number of these lines increased by 100, 121 and 147% for 14-day-old seedlings, respectively (FIG. 6); and 24, 38 and 48% for matured plants (FIG. 4B), respectively, as compared with NT. Plant height of lines A141E, G343A and GA2ox6-WT were 58, 44 and 30% of NT plants for 14-day-old seedlings, respectively (FIG. 6B), and 64, 40 and 19% for matured plants, respectively, as compared with NT. (FIG. 4A). Our previous study indicates that GA deficient rice plants produce more adventitious roots (Lo et al., 2008); the lines A141E and G343A still keep the more root number traits, which is increased in 14, 36 and 48% for 14-day-old seedlings, respectively (FIG. 6D), but the root length has no significant difference (FIG. 6E). Therefore, the shoot and root biomass in transgenic plants was determined. In 20-day-old seedlings of lines A141E and G343A, total biomasses were unchanged, but shoot weights were generally decreased and root weights increased, as compared with NT (FIG. 7). Overall, lines A141E had slightly, and G343A had significantly, lower shoot to root ratio than NT (FIG. 6C).

2.3 Grain Yield is Increased in GA Deficient Transgenic Rice Overexpressing A141E GA2ox6

Lines A141E and G343A possessed several good agronomic traits, such as semidwarf, higher tiller number, root number, and lower shoot to root ratio; we further evaluated the yield exhibition in field for more than two cropping season. The higher tiller number of GA deficient lines A141E and G343A showed almost all tillers are effective tillers (FIG. 8B); besides the panicle length, panicle weight and grain weight are similar to NT (FIG. 8C, 8D, 8E). All the above traits together resulted in the yield of line A141E increased significant by 23%, and of lines G343A and GA2ox6-WT reduced to 90 and 47%, respectively, as compared with NT (FIG. 8A). Each transgenic line exhibited similar characteristics in field growth conditions up to the T3 generation, indicating the genetic stability of GA defective phenotypes. In summary, 23% of yield increasement in lines A141E is due to increase in effective tiller numbers by 24%, as compared with the wild type rice.

2.4 Chlorophyll Content and Photosynthesis Rate are Increased in GA Deficient Rice The biomass evaluation showed GA deficient transgenic lines A141E and G343A have similar total fresh biomass but lesser dried total biomass (FIG. 7); which imply lines A141E and G343A have higher water content (FIG. 9C). To advanced evaluate the water consumption, all GA deficient lines had higher water use efficiency (WUE) than NT, which is increased by 42, 47, and 74% for lines A141E, G343A and GA2ox6-WT, respectively, as compared with NT (FIG. 9A). Moreover the water consumption is much lower than NT (40 to 56% lower than NT, FIG. 9B)

GA deficient transgenic plants displayed dark green leaves during the entire developmental stages, which prompted us to measure the chloroplast content and photosynthesis rate of transgenic lines A131E and G343A grown in field. The first fully expanded leaf before heading (80-day-old plants) was used to determine the chlorophyll content. Both chlorophyll a and b were increased, which resulted in the increase in total chlorophyll content in all transgenic lines (FIG. 9F-H). The morphology of leaves in GA deficient transgenic lines appeared more compact as compared with NT. Therefore, cell density in leaves was determined. The mesophyll cell density was significantly higher in all GA-deficient lines (FIG. 9D). The photosynthesis rate, as measured for CO2 consumption by LI-6400 (Wang et al., 2007), in these lines was also found to increase significantly (FIG. 9E).

2.5 Proline Level and Antioxidant Expression are Elevated in GA Deficient Rice

Our preliminary observation indicated that GA deficient rice lines were more tolerant to drought stresses. Therefore, stress tolerance was evaluated in 14-day-old seedlings by determining survival rates after various abiotic stress treatments. Lines A141E had slightly, and G343A and GA2ox6-WT had significantly, enhanced tolerance to dehydration (air-dry), 200 mM salt, heat (42° C.), and cold (4° C.) stresses (FIG. 10A-D).

Accumulation of the amino acid proline is induced in many plant species in response to environmental stresses, and which has been proposed to play an important role in osmotic adjustment and alleviation of oxidative stress damage caused by salt and water stresses (Szabados and Savoure, 2010; Sperdouli and Moustakas, 2012). Abiotic stresses also induce the formation of toxic reactive oxygen species (ROS) that cause protein and membrane damage, and efficient scavenging of ROS by ascorbate peroxidase (APX) and catalase play significant roles in the osmotic tolerance in plants (Hasegawa et al., 2000; Apel and Hirt, 2004). To understand the basis of abiotic stress tolerance in GA deficient plants, the level of proline and total peroxides and activities of catalase and ascorbate peroxidase (APx) were determined and compared in 14-day-old seedlings of lines A141E and G343A incubated under normal and dehydration conditions. The proline level and catalase and APx activities in lines A141E and G343A were significantly higher than NT under both normal and dehydration conditions, and generally higher in line G343A than in line A141E (FIGS. 10E, 10F and 10G). In contrast, both transgenic lines had less total peroxides level than NT (FIG. 10H).

3. DISCUSSIONS 3.1 the $C_{20}$ GA2oxs Among Different Species Plants

GA2oxs plays catabolic role for bio-active GAs and upstream compounds of GA biosynthesis pathway. GA2oxs form a small gene family and most of them are $C_{19}$ GA2oxs in different species of plants (Sun and Gubler, 2004; Yamaguchi, 2008). The previous studies showed GA2oxs in genome are not functional redundantly; some GA2oxs have distinct expression profile, response to environmental stress and function. For example, $C_{19}$ GA2oxs play major homeostasis regulation of GA content in rice and *Arabidopsis* (Sakai et al., 2003; Rieu et al., 2008); AtGA2ox2 is important in suppression of seeds germination of dark condition in *Arabidopsis* (Yamauchi et al., 2007); AtGA2ox7 play the crucial role in regulation of gibberellins content under high-salinity stress (Magome et al., 2008b). The expression profile of rice $C_{20}$ GA2ox6 is co-related with germination and tillering development (Lo et al., 2008). The findings indicated the $C_{20}$ GA2oxs also play important role in development and stress regulation. However, after six $C_{20}$ GA2oxs—AtGA2ox7, AtGA2ox8, SoGA2ox3, OsGA2ox5, OsGA2ox6 and OsGA2ox9 were identified (Schomburg et al., 2003; Lee and Zeevaart, 2005; Lo et al., 2008), fewer study discussed about $C_{20}$ GA2oxs, except one putative $C_{20}$ GA2ox gene from soybean were identified by blast analysis (Han and Zhu, 2011). Three unique conserved motifs were identified in $C_{20}$ GA2oxs; only the motif II is rendered to associate with substrate binding site because of the sequence is similar to that of GA20oxs (Lee and Zeevaart, 2005; Lo et al., 2008). No further study discussed about the function of the three conserved motifs and other $C_{20}$ GA2ox genes.

Mutants or transgenic rice overexpressing class $C_{20}$ GA2oxs, under the control of their native or a constitutive promoter, exhibited broad range mutant phenotypes, depending on promoters and GA2ox genes. In addition to some known effects caused by overexpression of GA2oxs, such as reduced plant height, small dark green leaves, delayed seed germination, delayed flowering, and reduced seed production, we also found thicker stem, early and increased tillering, more active adventitious root growth, and altered root architecture due to reduced accumulation of bioactive GA. These revealed that plants growth are significantly affected by GA content in rice was regulated by expression level and different group of GA2oxs. These studies suggest the pleiotropic role of GA2oxs in controlling rice growth and architecture. We found that $C_{20}$ GA2oxs caused less severe GA-defective phenotypes than $C_{19}$ GA2oxs, for example, overexpressed GA2ox1 or GA2ox3 severely retard the vegetative and reproductive development during the whole life span. We also identified a functional motif necessary for activity of the class $C_{20}$ GA2oxs (Lo et al., 2008).

To realize any other $C_{20}$ GA2oxs exists in plants, we further use the 30 identified amino acids from three unique conserved motifs of OsGA2ox6 to blast against NCBI and TIGR database (blast.ncbi.nlm.nih.gov/; rice.plantbiology.msu.edu/). More than 12 putative $C_{20}$ GA2oxs genes were identified from 8 different species (Supplemental Table 6); it revealed that $C_{20}$ GA2oxs widely existed in plant genome, and there should be at least one to three $C_{20}$ GA2oxs in all plant species; even though the $C_{20}$ GA2oxs is not responsible to GA homeostasis regulation, those genes may play important role in particular regulation or physiological function. The alignment of 12 new searched $C_{20}$ GA2oxs with former 6 $C_{20}$ GA2oxs and 23 $C_{19}$ GA2oxs; the phylogenetic tree is significantly separated into two groups by $C_{19}$ and $C_{20}$ type (FIG. 1). This indicated the GA2oxs were highly conserved among $C_{19}$ and $C_{20}$ type despite of the species difference. Among $C_{20}$ group, OsGA2ox6 and OsGA2ox9 were much more similar to the $C_{20}$ GA2oxs from monocots than those from dicots (AtGA2ox7, AtGA2ox8, and SoGA2ox3); for example OsGA2ox6 is grouped with Bd-1438, Sb-8199 and Zm-5669 (from *Brachypodium distachyon, Sorghum bicolor* and *Zea mays*) and OsGA2ox9 is grouped with Bd-5413 and Hv-2832 (from 2q*Brachypodium distachyon* and *Hordeum vulgare*) in phylogenetic tree. Besides, the similarity between $C_{20}$ GA2oxs is higher than that of $C_{19}$ GA2oxs, this may contributed by the extra conserved motifs beyond the 2-ODD domain of all GA2oxs (FIG. 2A and FIG. 1).

Figure 2:
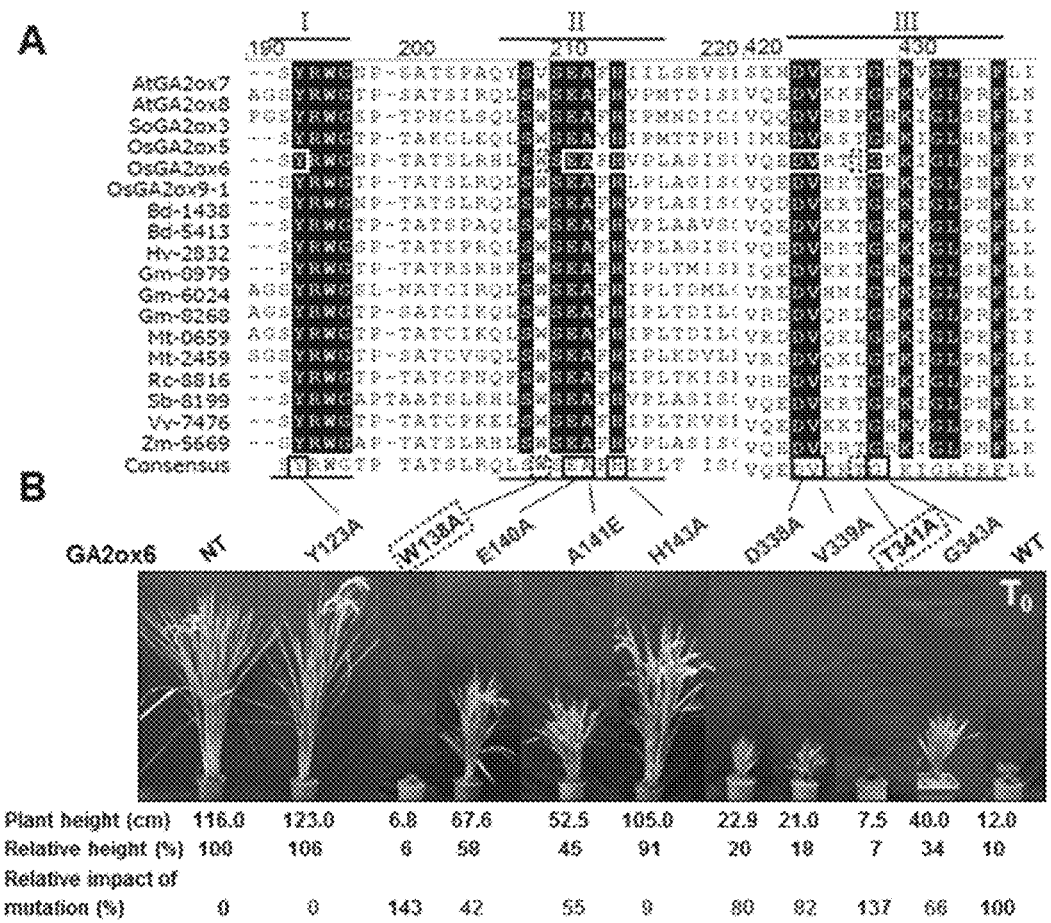
FIG. 2 shows certain amino acids in three conserved motifs are essential for functions of $C_{20}$ GA2oxs in rice. (A) Amino acid sequence alignment of $C_{20}$ GA2oxs from different plant species. Roman numerals above sequences indicate the three unique and conserved motifs present in $C_{20}$ GA2oxs. Identical amino acid residues are highlighted in white on black background. Underlines denote the conserved 30 amino acids in motifs I, II and II of $C_{20}$ GA2oxs. Point mutations were conducted with the rice GA2ox6 (OsGA2ox). Mutations effective and ineffective in reducing GA2ox6 activity in transgenic rice are marked by solid-line squares and dotted-line squares, respectively. SEQ ID NOs: 66-84; from top to bottom. (B) Photos of 3-month-old T0 generation of non-transgenic (NT) rice and 11 transgenic lines overexpressing point-mutated GA2ox6s. The average and relative plant height and relative impact of mutation (%) of each transgenic line are indicated below photos. Mutants Y123A, H143A, E140A, A141E, and G343A were highly or moderately effective in reducing GA2ox6 activity in transgenic rice. (C) The accumulation of mRNA of point-mutated GA2ox6 in transgenic rice was determined by RT-PCR. The 18S rRNA was used as RNA loading control. Upper panel: T0 generation of transgenic line. Lower panel: T1 generation of transgenic line.

In previous study revealed that modulate GA2oxs expression level to regulate GA level in plants by RNAi approach, differential or inducible promoter and/or biological activities of GA2oxs could apparently alter the plant architecture and biomass (Curtis et al., 2005; Dayan et al., 2010). To modulate the $C_{20}$ GA2oxs enzyme activity will also give rise to some beneficial phenotypes in rice, including semi-dwarfism, thicker stem, increased root system, early tillering, and higher tiller numbers that may favor grain yield (Lo et al., 2008). In present study, we are the first one to modulate the variant levels of $C_{20}$ GA2oxs enzyme activity in rice. We did eleven overexpression of point mutated GA2ox6 transgenic with single mutated amino acid as indicated in FIG. 2. We successfully got Y123A (motif I), E140A, A141E (motif II), H143A (motif II), and G343A (motif III) 5 transgenic plants; the amount of the bioactive gibberellins compound is reduced in different extent by overexpressed GA2ox6 gene with point mutation in rice. GA2ox6 enzyme activity is fully lost or reduced in different level (FIG. 2B). It implies 5 a.a. including Y123, E140, A141, H143, and G343 may be important for function of GA2ox6.

3.2 the Critical Amino Acids Among Three Conserved Motifs in $C_{20}$ GA2oxs Among Different Species Plants Amino acids alignment among 18 $C_{20}$ GA2oxs showed all $C_{20}$ GA2oxs possess three conserved motifs (FIG. 2A). Interestingly, conserved motif I is identical among 18 $C_{20}$ GA2oxs except the Gm-8979. However, the function of conserved motif I is still unknown. We further found that more amino acids flanking to these three conserved motifs were highly conserved among 18 $C_{20}$ GA2oxs. There are 16 over 30 amino acids in three conserved motifs were almost high identity among all predicted $C_{20}$ GA2oxs, these 16 amino acids may be important for the function of $C_{20}$ GA2oxs. See Table 2 below.

TABLE 2

Identity comparison (%) of 3 conserved motifs among rice $C_{20}$ GA2oxs.

| | AtGA2ox7 | AtGA2ox8 | SoGA2ox3 | OsGA2ox5 | OsGA2ox6 | OsGA2ox9 |
|---|---|---|---|---|---|---|
| | | | Motif I (5 a.a.) | | | |
| AtGA2ox7 | 100 | 100 | 100 | 100 | 100 | 100 |
| AtGA2ox8 | | 100 | 100 | 100 | 100 | 100 |
| SoGA2ox3 | | | 100 | 100 | 100 | 100 |
| OsGA2ox5 | | | | 100 | 100 | 100 |
| OsGA2ox6 | | | | | 100 | 100 |
| OsGA2ox9 | | | | | | 100 |
| | | | Motif II (11 a.a.) | | | |
| AtGA2ox7 | 100 | 54 | 64 | 54 | 64 | 64 |
| AtGA2ox8 | | 100 | 91 | 82 | 91 | 82 |
| SoGA2ox3 | | | 100 | 91 | 82 | 82 |
| OsGA2ox5 | | | | 100 | 73 | 73 |
| OsGA2ox6 | | | | | 100 | 91 |
| OsGA2ox9 | | | | | | 100 |
| | | | Motif III (14 a.a.) | | | |
| AtGA2ox7 | 100 | 71 | 71 | 64 | 57 | 71 |
| AtGA2ox8 | | 100 | 64 | 57 | 57 | 64 |
| SoGA2ox3 | | | 100 | 71 | 64 | 57 |
| OsGA2ox5 | | | | 100 | 71 | 57 |
| OsGA2ox6 | | | | | 100 | 71 |
| OsGA2ox9 | | | | | | 100 |

Therefore, it could be re-configured the conserved sequence in three unique motifs as I: xYRWG (SEQ ID NO: 2), II: xxSxSEAxHxxx (SEQ ID NO: 3), and III: DVxxxGxKxGLxxF (SEQ ID NO: 4) (FIG. 2A). There is no any study to unravel the role of those amino acids in these motifs and the function of three conserved motifs. This study is the first one to identify the importance of those amino acids. The transgenic rice showed mutation on Y123, E140, A141, H143, and G343 were effective mutations (FIG. 2B). However, these 5 amino acids were the identical amino acids reside within the 3 conserved motifs (FIG. 1A). This also demonstrated the 16 amino acids may be the critical amino acids for $C_{20}$ GA2oxs function.

3.3 Moderate Semi-Dwarf Rice Mutant Produced by Reduce GA Content Resulted High Yield Potency From the green revolution era, all the crop breeders or researchers focused on the searching the best "New Plant Type" (NPT) to solve the food shortage (Sasaki et al., 2002; Jeon et al., 2011). The widely adapted NPT is proposed to be slightly low tillering, no unproductive tillers, more grains per panicle, dark green, thick and erect leaves, and a vigorous and deep root system. For example, both gain of function of DEP1 and overexpress SPL14 could result lesser tillers, high grain number, and high yield mutants (Huang et al., 2009; Jiao et al., 2010; Miura et al., 2010).

Figure 3:
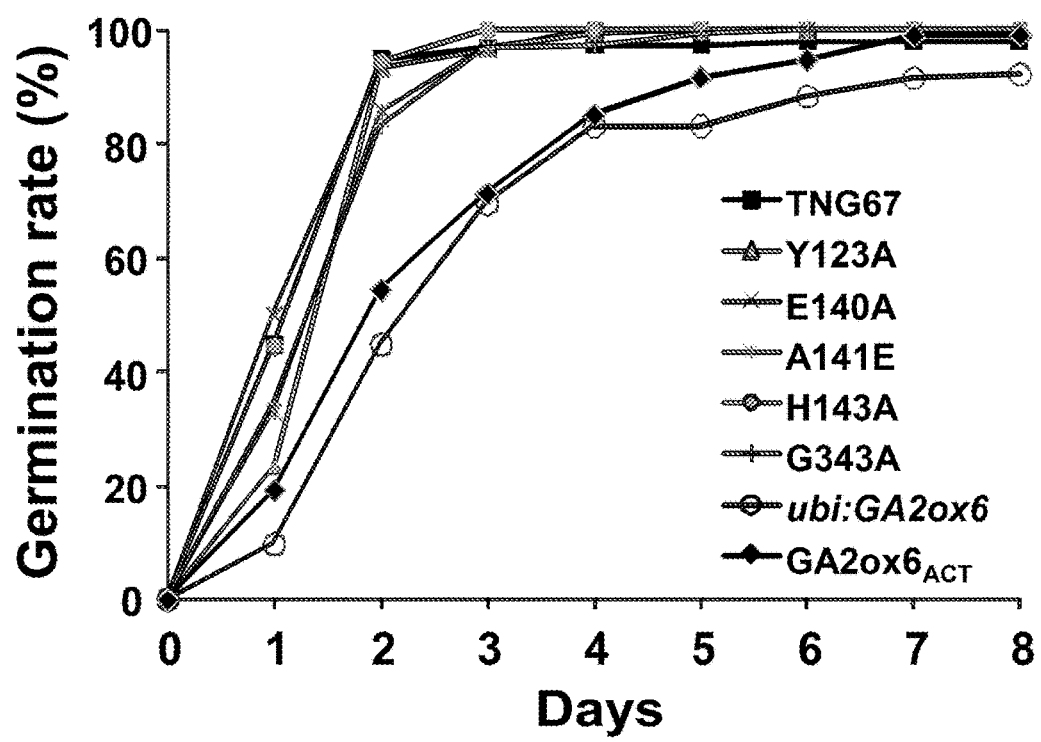
FIG. 3 shows seed germination rates, with n=154, 30, 30, 154, 54, 154, 154, 100 for transgenic lines overexpressing NT, Y123, E140, A141, H143, G343 and intact GA2ox6 (WT), respectively.
Figure 8:
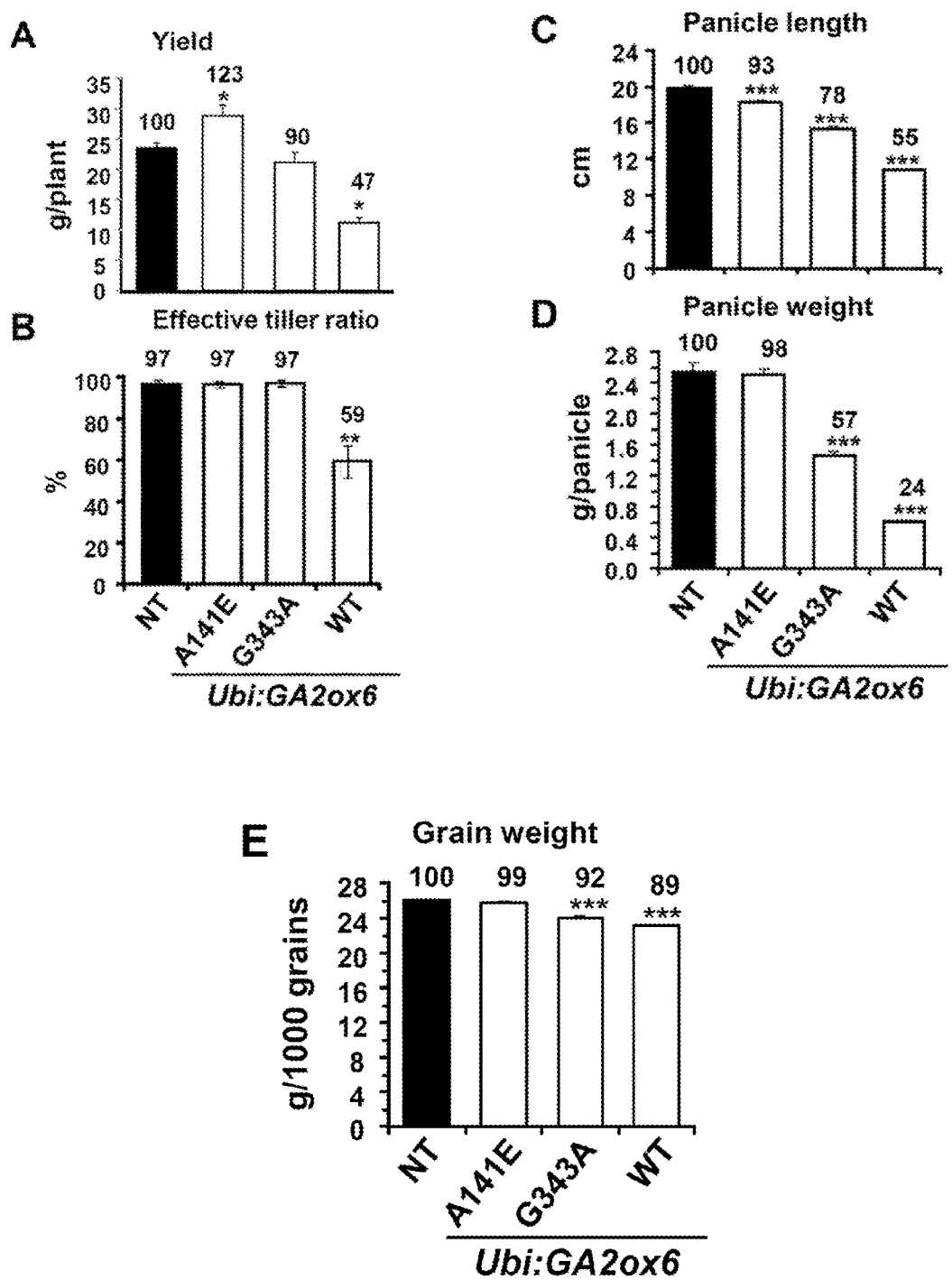
FIG. 8 GA deficient transgenic rice overexpressing A141E GA2ox6 exhibits increased grain yield in field. (A) Total yield for each plant. (B) Effective tiller ratio. (C) Panicle length. (D) Panicle weight. (E) Thousand grains weight. Error bars indicate standard error of the mean, SEM. n=17, 19, 19, and 26 for NT, A141E, G343A and WT GA2ox6. Difference was compared between transgenic lines and WT. Significance levels: * P<0.05,  P<0.01, * P<0.001.

In this study, we reduced the GA content by overexpression of GA2ox6 with point mutated on GA2ox6 to a moderate content (A141E) led to a slightly dwarf (36% shorter than wild type-TNG67) and also slightly shorter panicle (93% of WT). This GA deficient mutant also exhibited 1.24 fold of tiller number with 97% of effective tillers and normal fertility; however, those combinatory factors resulted in 23% increase of total yield (FIG. 8, FIG. 4). The moderate GA deficient mutant-A141E, still keep the typical GA deficient phenotype, such as darker green leaves thicker stem and erect leaves and stem. The slow in germination and flowering morphology were rescued by the partially loss of GA2ox6 enzyme activity (FIG. 3, FIG. 5).

In our study, we got the transgenic rice with moderate regulated GA content in vivo, it possess the desired GA deficient advantages (semi-dwarf, more tillers, thicker stem, more and thicker roots, dark green leaves, and erect plant architecture) but no unfavorable defects (slow in germination and flowering, low yield). This data demonstrate we could get high tillering high yield NPT of rice by regulating the GA content through $C_{20}$ GA2ox6 function.

3.4 Moderate GA Deficient Rice Mutant Possess High Stress Tolerant with Only Slightly Reduction in Yield The mechanism for plant to response to abiotic stress is complicated and many proteins involve in variable pathway. Proteomics and transcriptomics is the popular method to get the whole picture (Sobhanian et al., 2011; Wang et al., 2011). ABA, ethylene, and IAA were broadly discussed on the response of abiotic stress. Recently, some studies find gibberellins metabolic and signaling pathway were also involve or response to the abiotic stress. For example, A recessive gibberellin (GA)-insensitive dwarf mutant of rice, gibberellin-insensitive dwarf1 (gid1), demonstrated gid1 is involved in tolerance to cold stress and resistance to blast fungus by regulating the PBZ1 protein (Tanaka et al., 2006). AtGA2ox2 and AtGA2ox8 were induced by UV-B (Ulm et al., 2004). OsGA2ox3 and OsGA2ox6 could be up-regulation under cold (4° C.) stress (Achard et al., 2008). AtGA2ox7 were up-regulated under salinity stress (Magome et al., 2008a); OsGA2ox8 is repressed in roots but and down-regulated in leaves under drought stress (Wang et al., 2011). Nowadays, to introduce. modulate or express stress defense genes using the transgenic approaches are the most feasible way to overcome the stress in several crops, including maize, rice soybean, wheat, barley, and common bean, etc. (Ashraf, 2009, 2010). There is no any cultivar or transgenic plant designed based on the regulation of GAs content.

Figure 10:
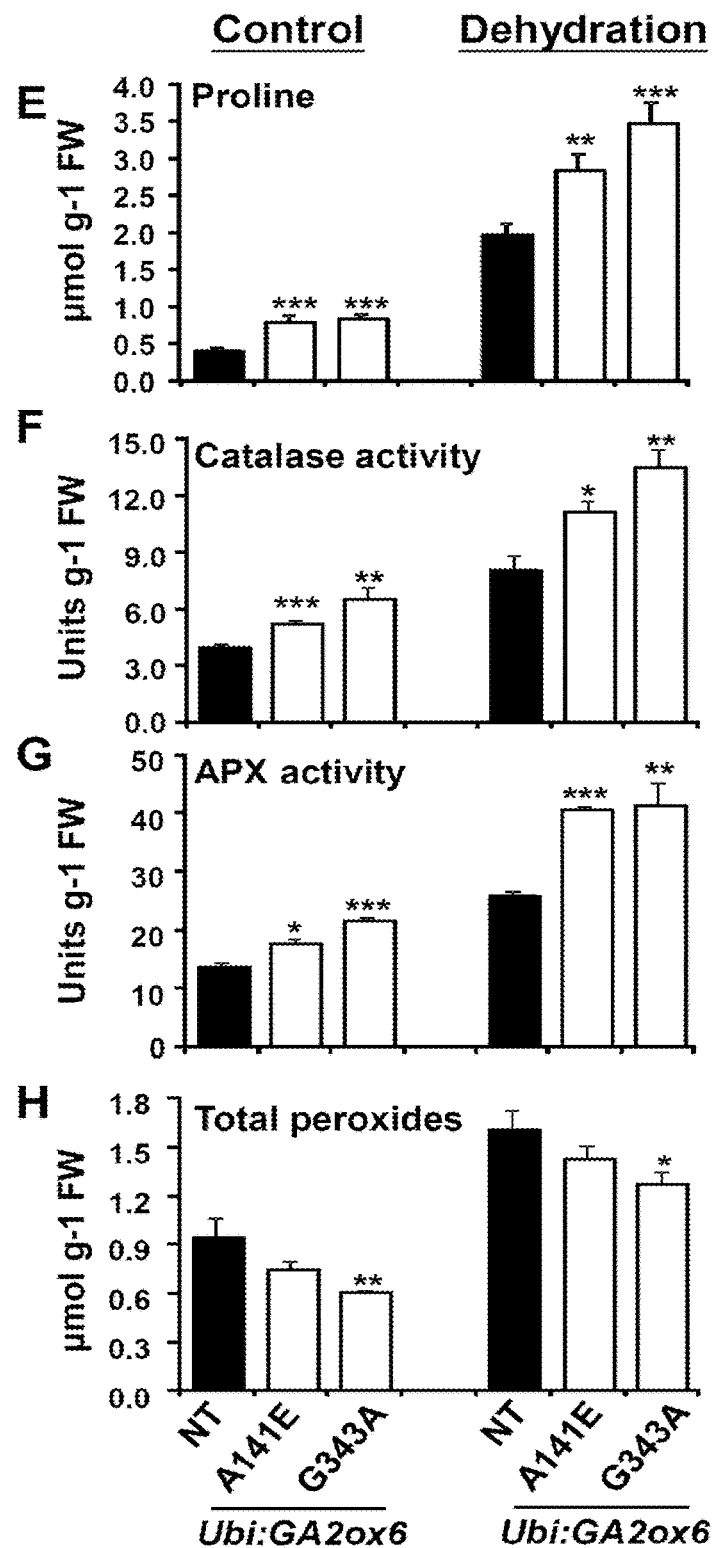
FIG. 10 shows that higher peroxides cleavage ability and osmotic protection molecule for GA deficient transgenic rice overexpressing A141E and G343A GA2ox6 lead to high potential of abiotic stress tolerance. 14-day-old seedlings were used for biochemical analysis; and were subjected to various abiotic stress treatment. Survival rates were determined after recovery from stress treatments for 6 days. (A) Dehydration for 6 h. (B) Salt (200 mM NaCl) treatment for 2 days. (C) Heat (42° C.) treatment for 2 days. (D) Cold (4° C.) treatment for 2 days. (E) Proline content. (F) Catalase activity. (G) Ascorbate peroxidase activity. (H) Total peroxides content. N=6 for number of seedlings for NT and lines overexpressing A141E, G343A, and WT GA2ox6 was 120, 49, 64, 77, 73 for drought treatment, 124, 74, 58, 99, 85 for salt treatment, 117, 44, 58, 74, 85 for cold treatment, and 134, 74, 69, 72, 56 for heat treatment, respectively. Error bars indicate standard error of the mean, SEM. Difference was compared between transgenic lines and WT. Significance levels: * P<0.05,  P<0.01, * P<0.001.

In this study, we proof the GA deficient mutant could suffer and survive well from multiple stresses, including drought (dehydration), salt (200 mM NaCl), cold (4° C.), and heat (42° C.) (FIG. 10). However, low yield phenomena always accompanies with the severely dwarfism. Here, we designed several overexpressed OsGA2ox6 by ubiquitin promoter with different point mutation on three conserved motifs. The $T_1$ transgenic progenies of 5 effective mutation on Y123, E140, A141, H143, and G343 (FIG. 2) with different level of GA deficient phenotype demonstrated the endogenous GA content is opposite to the stress tolerant potency; the difference of tolerance was the most obviously under dehydration treatment, and only mild difference was observed under cold stress (FIG. 10). Among these 5 effective mutations, G343A showed significantly higher stress tolerant potency, similar to that of Ubi:GA2ox6 transgenic rice; the most important is total yield of G343A did not showed significant lower than that of WT (FIG. 8). This transgenic rice possesses highly potential for developing into a good variety for planting on the adverse circumstances.

Figure 9:
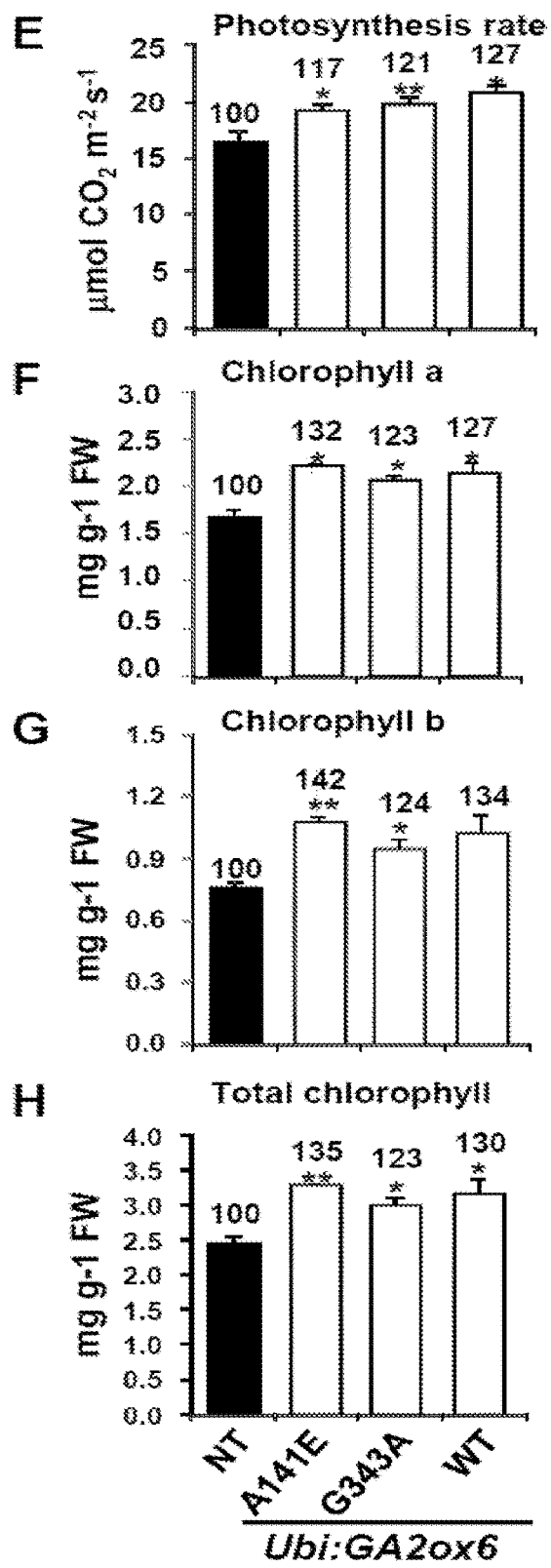
FIG. 9 GA deficient transgenic rice overexpressing A141E and G343A GA2ox6 exhibits higher water use efficiency (WUE), water content, photosynthesis rate and chlorophyll contents related to higher cell density in GA deficient plants. (A) WUE: mg of dried biomass increasement/ml water consumption/plant/day. (B) Water consumption: ml of water use/day/plant. (C) Water content percentage of total fresh biomass. (D) Cell density. (E) Maximum photosynthesis rate. (F) Chlorophyll a content. (G) Chlorophyll b content. (H) Total chlorophyll content. WUE, water consumption, and water content were measured from 20-day-old plants. Chlorophyll contents and cell density were measured from the $1^{st}$ expanded leaf before heading stage; cell number per $mm^2$ were counted from the mesophyll cells between small veins. Photosynthesis rate were detected at 60-day-old plants (highly tillering stage). Error bars indicate standard error of the mean, SEM. n=3 for A, B, C; n=12 for D; and n=6 for E, F, G, and H for each transgenic line. Difference was compared between transgenic lines and WT. Significance levels: * P<0.05,  P<0.01, * P<0.001.

3.5 GA Deficient Resulted in High Stress Tolerance by Alter the Root System, Water Consumption, Water and Chlorophyll Content In present study, the GA deficient plants were regulated by $C_{20}$ GA2oxs in various levels; moderate GA deficient level alters root development, reduces the shoot to root ratio, which contribute to lesser water loss, higher water use efficiency and the higher stress tolerant potency (FIG. 9, FIG. 10).

To date, rare is known about the relationship between endogenous GA concentration and chlorophyll content. However, several conflict theories were proposed about the effect of GA on the chlorophyll content (Poovaiah and Leopold, 1973; Perez et al., 1974; Ougham et al., 2001; Foo et al., 2006; Stavang et al., 2010; Hudson et al., 2011). In our study, both chlorophyll a and b contents are significantly increased in GA deficient plants; which may able to interpret that dark green leaves. However, several drought resistance varieties contain higher chlorophyll content (Guo et al., 2009; Luo, 2010). The increase in chlorophyll content may be the factor in promoting the photosynthesis rate and nitrogen utility, thus result in yield increase.

Water stress is the most serious cause for the yield loss of crops. However, breeding of mutants exhibit high dehydration avoidance, dehydration tolerance, and dehydration recovery is an import and urgent mission for the food security worldwide. For the abovementioned perspective, plants with stronger root system, higher water content, lower water consumption, closure of stomata, thicker peduncle neck, lesser shoot to root ratio, and higher chlorophyll content were the idea type for crop plants (Luo, 2010; Yu et al., 2012). In our present study, different level of GA deficient plants, including G343A, Ubi:GA2ox6 and GA2ox6$_{ACT}$, could fit in with all above mentioned traits and result in higher multiple stress tolerance, especial for dehydration stress. The most interesting is moderate reduce of endogenous GA level by overexpressed GA2ox6 with point mutation could successful get the idea high stress tolerant transgenic plants but not significant reduction in grain yield.

3.6 Moderate GA Deficient Rice Mutant Possess High Ability in Scavenging of Peroxides and Cellular Homeostasis Under Normal and Stress Environment Abiotic stresses cause a series of physiological response in plants to escape, avoid and survive from the stress attack. Response of drought stress is complex and regulated by a large number of genes without any master regulator system (Seki et al., 2007; Fukao and Xiong, 2013). Oxidative stress and osmotic imbalance are the major crises under drought stress, which may cause programmed cell death for plants (Huang et al., 2012; Fukao and Xiong, 2013). Nowadays, superoxide dismutase (SOD), catalase (CAT), and ascorbate peroxidase (APX) were well known to be the major enzymes in the ROS scavenging enzymatic antioxidants (Cruz de Carvalho, 2008; Gill and Tuteja, 2010). Only fewer studies revealed the relationship between gibberellins and ROS (Cheminant et al., 2011; Ishibashi et al., 2012), rare is known directly about the gibberellins level and the ability or mechanism of ROS scavenging, our study showed different levels of GA deficiency elevated the CAT and APX enzyme activity in relative levels under both control and dehydration environment; which further decreased the total peroxides level in plants under both conditions for G343A and higher survival rate for G343A from dehydration stress (FIG. 10F to 10H).

Proline plays a multifunctional role in stress defense mechanisms, such as osmolyte, protection of protein integrity, signaling molecule, influence of cell proliferation or cell death, ROS scavenging (Seki et al., 2007; Szabados and Savoure, 2010). Some studies had demonstrated that elevation of endogenous proline content or exogenous proline treatment could enhance the stress tolerant and ROS scavenging by increasing the enzyme activities of SOD, CAT and APX (Szekely et al., 2008; Nounjan et al., 2012). In present study, we revealed the GA level influenced the endogenous proline level; and further directly or indirectly regulated the SOD, CAT (FIG. 10). APX and peroxides in plants under the normal and dehydration condition. Thus, we could generate a good new plant—G343A to tolerant the various stress condition.

4. CONCLUSIONS

In summary, to control the moderate endogenous GA level in plants, we provide five effective mutations (Y123A, E140A, A141E, H143A and G343A) to reduce GA2ox6 enzymatic activity to different extents, which led to various degrees of GA deficient yet beneficial agronomic traits, at least including semidwarfism and increase in tiller number and chlorophyll density, decrease in shoot to root ratio, and enhancement of water use efficiency in transgenic rice. Particularly, among them, we got one high multiple stress tolerant transgenic rice with semi-dwarf, high tillering, stronger root system, lower water consumption, higher water content, and dark green, erect leaves—G343A. We also got one high multiple stress tolerant transgenic rice with semi-dwarf, high tillering, stronger root system, lower water consumption, higher water content, and dark green, erect leaves—G343A. The appropriate lower GA level can turn on the whole stress defense mechanism, including the non-enzymatic (proline) and enzymatic systems (APX, CA) to get higher stress tolerance but without significant yield penalty. Both transgenic plants will be high economically valuable and high potential utility after the more clear characterization and domestication in the future to control the moderate endogenous.

Sequence Information

```
>AlGA2ox7 (SEQ ID NO: 18)
MASQPPFKTNFCSIFGSSFPNSTSESNTNTSTIQTSGIKLPVIDLSHLTSGEEVKRK

RCVKQMVAAAKEWGFFQIVNHGIPKDVFEMMLLEEKKLFDQPFSVKVRERFSDLSKN

SYRWGNPSATSPAQYSVSEAFHIILSEVSRISDDRNNLRTIVETYVQEIARVAQMIC

EILGKQVNVSSEYFENIFELENSFLRLNKYHPSVFGSEVFGLVPHTDTSFLTILSQD

QIGGLELENNGQWISVKPCLEALTVNIGDMFQALSNGVYQSVRHRVISPANIERMSI

AFFVCPYLETEIDCFGYPKKYRRFSFREYKEQSEHDVKETGDKVGLSRFLI

>AtGA2ox8 (SEQ ID NO: 19)
MDPPFNEIYNNLLYNQITKKDNDVSEIPFSFSVTAVVEEVELPVIDVSRLIDGAEEE

REKCKEAIARASREWGFFQVINHGISMDVLEKMRQEQIRVFREPFDKKSNSTMEKFA

SESEALAYMLAEVLAEKSGQNSSFFKENCVRNTCYLRMNRYPPCPKPSEVYGLMPHT

DSDFLTILYQDQVGGLQLIKDNRWIAVKPNPKALIINIGDLFQAWSNGMYKSVEHRV

MTNPKVERFSTAYFMCPSYDAVIECSSDRPAYRNFSFREFRQQVQEDVKKFGFKVGL

PRFLNHVY

>SoGA2ox3 (SEQ ID NO: 20)
MASTKVVEHLKENVLWKQAIMDRNANISDPPFEETYKNLLLKHNITPLTTTTTTTTTATIE

VRDLPLIDLSRLVATAAKERENCKRDIANASREWGFFQVVNHGIPHRMLEEMNKEQVKVFRE

PFNKKKGDNCMNLRLSPGSYRWGSPTPNCLSQLSWSEAFHIPMNDICSNAPRNIANGNPNIS

NLCSTVKQFATTVSELANKLANILVEKLGHDELTFIEEKCSPNTCYLRMNRYPPCPKYSHVL

GLMPHTDSDFLTILYQDQVGGLQLVKDGRWISVKPNPEALIVNIGDLFQAWSNGVYKSVVHR

VVANPRFERFSTAYFLCPSGDAVIQSYREPSMYRKFSFGEYRQQVQQDVREFGHKIGLSRFL

IC

>OsGA2ox5 (SEQ ID NO: 21)
MEEHDYDSNSNPPLMSTYKHLFVEQHRLDMDMGAIDVDECELPVIDLAGLMEAEQVC

RADMVRAASEWGFFQVTNHGVPQALLRELHDAQVAVFRRPFQEKVTERLLGFSPESY

RWGTPTAKCLEQLSWSEAYHIPMTTPRPSTSIRARAVIEEVSRAMYELAQKLAEILM

RGLPGAGEGETMVTTREETCFLRLNRYPPCAMAMGGFGLCPHTDSDLLTIVHQQQDT

VGGLQLLKGGRWVAVKPSPSTLIVNVGDLLQAWSNDVYKSVEHRVMANATLERFSMA

FFLCPSYHTLIIPSSSHVHDDDAHYRSFTFGEYRKQIMEDVRSTGRKIGLHRFRTR
```

>OsGA2ox9 (SEQ ID NO: 22)
MPAIADCAADPPLADSYYTLLRLGGDDDDDACTKVTTTPQPVSECELPMIDVGCLTA

PTGAAAAAAVGQQHQAEERAACAAAIAAAAAEWGFFQVVNHGVAQELLEAMRREQAR

LFRLPFEAKSSAGLLNDSYRWGTPTATSLRQLSWSEAFHLPLAGISGKSCNYGDLTS

LRDVTREVADAMSRLARALARVLAESLLGHAAGERFPEGCDDATCFLRLNRYPPCPF

PPDDAFGLVPHTDSDFLTVLCQDHVGGLQLMKGSRWVAVKPIPGALIVNIGDLFQAW

SNNRYKSVEHRVMTNATTERYSVAYFLCPSYDSPIGTCREPSPYKAFTFGEYRRRVQ

EDVKKTGKKTGLSNFLV

>GA20x6-WT (SEQ ID NO: 1)
MPAFADIAIDPPLADSYRALALLRRDRDGGIAPPAVQMVGSGGAVLERDLPMVDLER

LTRGGAGERKACAGAMARAASEWGFFQLTNHGVGRELMEEMRREQARLFRLPFETKE

KAGLLNGSYRWGNPTATSLRHLSWSEAFHVPLASISGADCDFGDLTSLRGVMQEVAE

AMSRVANTVAAALAEELTGRGGGGASAAPWFPAGCDETTCFLRLNRYPACPFAADTF

GLVPHTDSDFLTVLCQDQVGGLHLMKDSRWVAVRPRPDALVVNIGDLFQAWSNNRYK

SVEHKVVANAKTDRLSVAYFLCPSYDSLVGTCGEPSPYRAFTFGEYRKKVQEDVRTT

GKKIGLPNFFKHSSVQ

>GA20x6 (Y123A) (SEQ ID NO: 8)
MPAFADIAIDPPLADSYRALALLRRDRDGGIAPPAVQMVGSGGAVLERDLPMVDLER

LTRGGAGERKACAGAMARAASEWGFFQLTNHGVGRELMEEMRREQARLFRLPFETKE

KAGLLNGSARWGNPTATSLRHLSWSEAFHVPLASISGADCDFGDLTSLRGVMQEVAE

AMSRVANTVAAALAEELTGRGGGGASAAPWFPAGCDETTCFLRLNRYPACPFAADTF

GLVPHTDSDFLTVLCQDQVGGLHLMKDSRWVAVRPRPDALVVNIGDLFQAWSNNRYK

SVEHKVVANAKTDRLSVAYFLCPSYDSLVGTCGEPSPYRAFTFGEYRKKVQEDVRTT

GKKIGLPNFFKHSSVQ

>GA20x6 (E140A) (SEQ ID NO: 9)
MPAFADIAIDPPLADSYRALALLRRDRDGGIAPPAVQMVGSGGAVLERDLPMVDLER

LTRGGAGERKACAGAMARAASEWGFFQLTNHGVGRELMEEMRREQARLFRLPFETKE

KAGLLNGSYRWGNPTATSLRHLSWSAAFHVPLASISGADCDFGDLTSLRGVMQEVAE

AMSRVANTVAAALAEELTGRGGGGASAAPWFPAGCDETTCFLRLNRYPACPFAADTF

GLVPHTDSDFLTVLCQDQVGGLHLMKDSRWVAVRPRPDALVVNIGDLFQAWSNNRYK

SVEHKVVANAKTDRLSVAYFLCPSYDSLVGTCGEPSPYRAFTFGEYRKKVQEDVRTT

GKKIGLPNFFKHSSVQ

>GA20x6 (A141E) (SEQ ID NO: 10)
MPAFADIAIDPPLADSYRALALLRRDRDGGIAPPAVQMVGSGGAVLERDLPMVDLER

LTRGGAGERKACAGAMARAASEWGFFQLTNHGVGRELMEEMRREQARLFRLPFETKE

KAGLLNGSYRWGNPTATSLRHLSWSEEFHVPLASISGADCDFGDLTSLRGVMQEVAE

AMSRVANTVAAALAEELTGRGGGGASAAPWFPAGCDETTCFLRLNRYPACPFAADTF

GLVPHTDSDFLTVLCQDQVGGLHLMKDSRWVAVRPRPDALVVNIGDLFQAWSNNRYK

SVEHKVVANAKTDRLSVAYFLCPSYDSLVGTCGEPSPYRAFTFGEYRKKVQEDVRTT

GKKIGLPNFFKHSSVQ

>GA20x6 (H143A) (SEQ ID NO: 11)
MPAFADIAIDPPLADSYRALALLRRDRDGGIAPPAVQMVGSGGAVLERDLPMVDLER

LTRGGAGERKACAGAMARAASEWGFFQLTNHGVGRELMEEMRREQARLFRLPFETKE

KAGLLNGSYRWGNPTATSLRHLSWSEAFAVPLASISGADCDFGDLTSLRGVMQEVAE

-continued

```
AMSRVANTVAAALAEELTGRGGGGASAAPWFPAGCDETTCFLRLNRYPACPFAADTF

GLVPHTDSDFLTVLCQDQVGGLHLMKDSRWVAVRPRPDALVVNIGDLFQAWSNNRYK

SVEHKVVANAKTDRLSVAYFLCPSYDSLVGTCGEPSPYRAFTFGEYRKKVQEDVRTT

GKKIGLPNFFKHSSVQ

>GA2ox6(G343A) (SEQ ID NO: 12)
MPAFADIAIDPPLADSYRALALLRRDRDGGIAPPAVQMVGSGGAVLERDLPMVDLER

LTRGGAGERKACAGAMARAASEWGFFQLTNHGVGRELMEEMRREQARLFRLPFETKE

KAGLLNGSYRWGNPTATSLRHLSWSEAFHVPLASISGADCDFGDLTSLRGVMQEVAE

AMSRVANTVAAALAEELTGRGGGGASAAPWFPAGCDETTCFLRLNRYPACPFAADTF

GLVPHTDSDFLTVLCQDQVGGLHLMKDSRWVAVRPRPDALVVNIGDLFQAWSNNRYK

SVEHKVVANAKTDRLSVAYFLCPSYDSLVGTCGEPSPYRAFTFGEYRKKVQEDVRTT

AKKIGLPNFFKHSSVQ
```

REFERENCES

Abiko, M., Ohmori, Y., and Hirano, H. Y. (2008). Genome-wide expression profiling and identification of genes under the control of the DROOPING LEAF gene during midrib development in rice. Genes Genet Syst 83, 237-244.

Apel, K., and Hirt, H. (2004). Reactive oxygen species: metabolism, oxidative stress, and signal transduction. Annu Rev Plant Biol 55, 373-399.

Ashikari, M., Sakakibara, H., Lin, S., Yamamoto, T., Takashi, T., Nishimura, A., Angeles, E. R., Qian, Q., Kitano, H., and Matsuoka, M. (2005). Cytokinin oxidase regulates rice grain production. Science 309, 741-745.

Bates, L. S., Waldren, R. P., and Teare, I. D. (1973). Rapid determination of free proline for water-stress studies. Plant and Soil 39, 205-207.

Botwright, T. L., Rebetzke, G. J., Condon, A. G., and Richards, R. A. (2005a). Influence of the gibberellin-sensitive Rht8 dwarfing gene on leaf epidermal cell dimensions and early vigour in wheat (*Triticum aestivum* L.). Ann Bot 95, 631-639.

Botwright, T. L., Rebetzke, G. J., Condon, A. G., and Richards, R. A. (2005b). Influence of the gibberellin-sensitive Rht8 dwarfing gene on leaf epidermal cell dimensions and early vigour in wheat (*Triticum aestivum* L.). Annals of botany 95, 631-639.

Carrera, E., Bou, J., Garcia-Martinez, J. L., and Prat, S. (2000). Changes in GA 20-oxidase gene expression strongly affect stem length, tuber induction and tuber yield of potato plants. Plant J 22, 247-256.

Curtis, I. S., Hanada, A., Yamaguchi, S., and Kamiya, Y. (2005). Modification of plant architecture through the expression of GA 2-oxidase under the control of an estrogen inducible promoter in *Arabidopsis thaliana* L. Planta 222, 957-967.

Dayan, J., Schwarzkopf, M., Avni, A., and Aloni, R. (2010). Enhancing plant growth and fiber production by silencing GA 2-oxidase. Plant Biotechnol J 8, 425-435.

Hajdukiewicz, P., Svab, Z., and Maliga, P. (1994). The small, versatile pPZP family of *Agrobacterium* binary vectors for plant transformation. Plant Mol Biol 25, 989-994.

Hartweck, L. M. (2008). Gibberellin signaling. Planta 229, 1-13.

Hasegawa, P. M., Bressan, R. A., Zhu, J. K., and Bohnert, H. J. (2000). Plant Cellular and Molecular Responses to High Salinity. Annual review of plant physiology and plant molecular biology 51, 463-499.

Hedden, P., and Phillips, A. L. (2000). Gibberellin metabolism: new insights revealed by the genes. Trends Plant Sci 5, 523-530.

Hedden, P., and Thomas, S. G. (2012). Gibberellin biosynthesis and its regulation. Biochem J 444, 11-25.

IRRI. (2010). Rice Policy—Why is it happening? beta.irri.org/solutions/index.php?option=com_content&task=view&id=15.

Jeon, J.-S., Jung, K.-H., Kim, H.-B., Suh, J.-P., and Khush, G. (2011). Genetic and Molecular Insights into the Enhancement of Rice Yield Potential. Journal of Plant Biology 54, 1-9.

Jia, Q., Zhang, X. Q., Westcott, S., Broughton, S., Cakir, M., Yang, J., Lance, R., and Li, C. (2011). Expression level of a gibberellin 20-oxidase gene is associated with multiple agronomic and quality traits in barley. Theor Appl Genet 122, 1451-1460.

Jiao, Y., Wang, Y., Xue, D., Wang, J., Yan, M., Liu, G., Dong, G., Zeng, D., Lu, Z., Zhu, X., Qian, Q., and Li, J. (2010). Regulation of OsSPL14 by OsmiR156 defines ideal plant architecture in rice. Nature genetics 42, 541-544.

Kato, M., and Shimizu, S. (1985). Chlorophyll Metabolism in Higher Plants VI. Involvement of Peroxidase in Chlorophyll Degradation. Plant and Cell Physiology 26, 1291-1301.

Khush, G. S. (1999). Green revolution: preparing for the 21st century. Genome 42, 646-655.

Komatsu, K., Maekawa, M., Ujiie, S., Satake, Y., Furutani, I., Okamoto, H., Shimamoto, K., and Kyozuka, J. (2003). LAX and SPA: major regulators of shoot branching in rice. Proc Natl Acad Sci USA 100, 11765-11770.

Krugel, T., Lim, M., Gase, K., Halitschke, R., and Baldwin, I. T. (2002). *Agrobacterium*-mediated transformation of *Nicotiana attenuata*, a model ecological expression system. Chemoecology 12, 177-183.

Kunkel, T. A. (1985). Rapid and efficient site-specific mutagenesis without phenotypic selection. Proceedings of the National Academy of Sciences of the United States of America 82, 488-492.

Lee, D. J., and Zeevaart, J. A. (2005). Molecular cloning of GA 2-oxidase3 from spinach and its ectopic expression in *Nicotiana sylvestris*. Plant Physiol 138, 243-254.

Li, F., Liu, W., Tang, J., Chen, J., Tong, H., Hu, B., Li, C., Fang, J., Chen, M., and Chu, C. (2010). Rice DENSE AND ERECT PANICLE 2 is essential for determining panicle outgrowth and elongation. Cell research 20, 838-849.

Li, Y., Fan, C., Xing, Y., Jiang, Y., Luo, L., Sun, L., Shao, D., Xu, C., Li, X., Xiao, J., He, Y., and Zhang, Q. (2011). Natural variation in GS5 plays an important role in regulating grain size and yield in rice. Nat Genet.

Lichtenthaler, H. K. (1987). Chlorophylls and carotenoids-pigments of photosynthetic biomembranes. Methods in Enzymology 148, 350-382.

Lo, S. F., Yang, S. Y., Chen, K. T., Hsing, Y. I., Zeevaart, J. A., Chen, L. J., and Yu, S. M. (2008). A novel class of gibberellin 2-oxidases control semidwarfism, tillering, and root development in rice. THE PLANT CELL 20, 2603-2618.

Miura, K., Ikeda, M., Matsubara, A., Song, X. J., Ito, M., Asano, K., Matsuoka, M., Kitano, H., and Ashikari, M. (2010). OsSPL14 promotes panicle branching and higher grain productivity in rice. Nature genetics 42, 545-549.

Mohanty, A., Kathuria, H., Ferjani, A., Sakamoto, A., Mohanty, P., Murata, N., and Tyagi, A. K. (2002). Transgenics of an elite indica rice variety Pusa Basmati 1 harbouring the codA gene are highly tolerant to salt stress. Theor Appl Genet 106, 51-57.

Nakano, Y., and Asada, K. (1981). Hydrogen Peroxide is Scavenged by Ascorbate-specific Peroxidase in Spinach Chloroplasts. Plant and Cell Physiology 22, 867-880.

Peng, J., Richards, D. E., Hartley, N. M., Murphy, G. P., Devos, K. M., Flintham, J. E., Beales, J., Fish, L. J., Worland, A. J., Pelica, F., Sudhakar, D., Christou, P., Snape, J. W., Gale, M. D., and Harberd, N. P. (1999). 'Green revolution' genes encode mutant gibberellin response modulators. Nature 400, 256-261.

Qiao, Y., Piao, R., Shi, J., Lee, S. I., Jiang, W., Kim, B. K., Lee, J., Han, L., Ma, W., and Koh, H. J. (2011). Fine mapping and candidate gene analysis of dense and erect panicle 3, DEPS, which confers high grain yield in rice (Oryza sativa L.). Theor Appl Genet 122, 1439-1449.

Sagisaka, S. (1976). The Occurrence of Peroxide in a Perennial Plant, Populus gelrica. Plant Physiol 57, 308-309.

Sakai, M., Sakamoto, T., Saito, T., Matsuoka, M., Tanaka, H., and Kobayashi, M. (2003). Expression of novel rice gibberellin 2-oxidase gene is under homeostatic regulation by biologically active gibberellins. Journal of Plant Research 116, 161-164.

Sakamoto, T., Miura, K., Itoh, H., Tatsumi, T., Ueguchi-Tanaka, M., Ishiyama, K., Kobayashi, M., Agrawal, G. K., Takeda, S., Abe, K., Miyao, A., Hirochika, H., Kitano, H., Ashikari, M., and Matsuoka, M. (2004). An overview of gibberellin metabolism enzyme genes and their related mutants in rice. Plant Physiol 134, 1642-1653.

Sasaki, A., Ashikari, M., Ueguchi-Tanaka, M., Itoh, H., Nishimura, A., Swapan, D., Ishiyama, K., Saito, T., Kobayashi, M., Khush, G. S., Kitano, H., and Matsuoka, M. (2002). Green revolution: a mutant gibberellin-synthesis gene in rice. Nature 416, 701-702.

Schomburg, F. M., Bizzell, C. M., Lee, D. J., Zeevaart, J. A., and Amasino, R. M. (2003). Overexpression of a novel class of gibberellin 2-oxidases decreases gibberellin levels and creates dwarf plants. Plant Cell 15, 151-163.

Sperdouli, I., and Moustakas, M. (2012). Interaction of proline, sugars, and anthocyanins during photosynthetic acclimation of Arabidopsis thaliana to drought stress. J Plant Physiol 169, 577-585.

Spielmeyer, W., Ellis, M. H., and Chandler, P. M. (2002a). Semidwarf (sd-1), "green revolution" rice, contains a defective gibberellin 20-oxidase gene. Proc Natl Acad Sci USA 99, 9043-9048.

Spielmeyer, W., Ellis, M. H., and Chandler, P. M. (2002b). Semidwarf (sd-1), "green revolution" rice, contains a defective gibberellin 20-oxidase gene. Proceedings of the National Academy of Sciences of the United States of America 99, 9043-9048.

Sun, T. P. (2008). Gibberellin metabolism, perception and signaling pathways in Arabidopsis. Arabidopsis Book 6, e0103.

Szabados, L., and Savoure, A. (2010). Proline: a multifunctional amino acid. Trends Plant Sci 15, 89-97.

Wang, J., Xing, D., Zhang, L., and Jia, L. (2007). A new principle photosynthesis capacity biosensor based on quantitative measurement of delayed fluorescence in vivo. Biosensors & bioelectronics 22, 2861-2868.

Wang, Y., and Li, J. (2005). The plant architecture of rice (Oryza sativa). Plant Mol Biol 59, 75-84.

Wang, Y., and Li, J. (2006). Genes controlling plant architecture. Curr Opin Biotechnol 17, 123-129.

Wang, Y., and Li, J. (2008). Molecular basis of plant architecture. Annu Rev Plant Biol 59, 253-279.

Yadav, S. K., Pandey, P., Kumar, B., and Suresh, B. G. (2011). Genetic architecture, inter-relationship and selection criteria for yield improvement in rice (Oryza sativa L.). Pak J Biol Sci 14, 540-545.

Yamaguchi, S. (2008). Gibberellin metabolism and its regulation. Annual Review of Plant Biology 59, 225-251.

Yi, G., Choi, J. H., Jeong, E. G., Chon, N. S., Jena, K. K., Ku, Y. C., Kim, D. H., Eun, M. Y., Jeon, J. S., and Nam, M. H. (2005). Morphological and molecular characterization of a new frizzy panicle mutant, "fzp-9(t)", in rice (Oryza sativa L.). Hereditas 142, 92-97.

---

What is claimed is:

1. An isolated polynucleotide that encodes a mutant class $C_{20}$ gibberellin 2-oxidase protein ($C_{20}$ GA2ox), wherein the mutant $C_{20}$ GA2ox protein includes an amino acid mutation selected from the group consisting of:
   (i) an amino acid residue corresponding to position 123 of SEQ ID NO: 1 substituted with Alanine (123A),
   (ii) an amino acid residue corresponding to position 140 of SEQ ID NO: 1 substituted with Alanine (140A),
   (iii) an amino acid residue corresponding to position 141 of SEQ ID NO: 1 substituted with Glutamate (141E),
   (iv) an amino acid residue corresponding to position 143 of SEQ ID NO: 1 substituted with Alanine (143A), and
   (v) an amino acid residue corresponding to position 343 of SEQ ID NO: 1 substituted with Alanine (343A).

2. The isolated polynucleotide of claim 1, wherein the mutant $C_{20}$ GA2ox protein comprises an amino acid sequence selected from the group consisting of SEQ ID NO: 8, SEQ ID NO: 9, SEQ ID NO: 10, SEQ ID NO: 11 and SEQ ID NO: 12.

3. The isolated polynucleotide of claim 1, comprising a nucleotide sequence selected from the group consisting of SEQ ID NO: 13, SEQ ID NO: 14, SEQ ID NO: 15, SEQ ID NO: 16 and SEQ ID NO: 17.

4. An expression vector comprising a nucleotide sequence that encodes a mutant class C20 gibberellin 2-oxidase protein (C20 GA2ox), wherein the mutant $C_{20}$ GA2ox protein includes an amino acid mutation selected from the group consisting of:
   (i) an amino acid residue corresponding to position 123 of SEQ ID NO: 1 substituted with Alanine (123A),
   (ii) an amino acid residue corresponding to position 140 of SEQ ID NO: 1 substituted with Alanine (140A),
   (iii) an amino acid residue corresponding to position 141 of SEQ ID NO: 1 substituted with Glutamate (141E),
   (iv) an amino acid residue corresponding to position 143 of SEQ ID NO: 1 substituted with Alanine (143A), and
   (v) an amino acid residue corresponding to position 343 of SEQ ID NO: 1 substituted with Alanine (343A).

5. A recombinant cell comprising the expression vector of claim 4.

6. The recombinant cell of claim 5, which is a recombinant plant cell or a recombinant *Agrobacterium* cell.

7. A transgenic plant comprising a transgene, wherein the transgene encodes a mutant class C20 gibberellin 2-oxidase protein ($C_{20}$ GA2ox), wherein the mutant $C_{20}$ GA2ox protein includes an amino acid mutation selected from the group consisting of:
   (i) an amino acid residue corresponding to position 123 of SEQ ID NO: 1 substituted with Alanine (123A),
   (ii) an amino acid residue corresponding to position 140 of SEQ ID NO: 1 substituted with Alanine (140A), (iii) an amino acid residue corresponding to position 141 of SEQ ID NO: 1 substituted with Glutamate (141E),
(iv) an amino acid residue corresponding to position 143 of SEQ ID NO: 1 substituted with Alanine (143A), and
(v) an amino acid residue corresponding to position 343 of SEQ ID NO: 1 substituted with Alanine (343A).

8. The transgenic plant of claim 7, wherein the mutant $C_{20}$ GA2ox protein comprises an amino acid sequence selected from the group consisting of SEQ ID NO: 8, SEQ ID NO: 9, SEQ ID NO: 10, SEQ ID NO: 11 and SEQ ID NO: 12.

9. The transgenic plant of claim 7, wherein the transgene comprises a nucleotide sequence selected from the group consisting of SEQ ID NO: 13, SEQ ID NO: 14, SEQ ID NO: 15, SEQ ID NO: 16 and SEQ ID NO: 17.

10. The transgenic plant of claim 7, wherein the transgenic plant is higher in height, or has a higher germination rate than a plant of the same genetic background transformed with the wild type class C20 GA2ox while being grown under the same conditions.

11. The transgenic plant of claim 7, wherein the transgenic plant has a height that is about 25% to 99%, 30% to 70%, or 40% to 60% of a non-transgenic plant of the same genetic background while being grown under the same conditions.

12. The transgenic plant of claim 7, wherein the transgenic plant exhibits higher tiller numbers, earlier tillering, increased root system, lower shoot to root ratio, more efficient water consumption, higher chlorophyll content, higher mesophyll cell density, higher photosynthesis rate, higher grain yield, higher anti-oxidant activity, or higher tolerance to environmental stress than a non-transgenic plant of the same genetic background while being grown under the same conditions.

13. The transgenic plant of claim 12, wherein the environmental stress is selected from the group consisting of drought, temperature, salinity and oxidative stresses.

14. A method for producing a transgenic plant of claim 7, comprising (a) transforming a plant cell with a nucleic acid molecule comprising the transgene to obtain a recombinant plant cell; and (b) growing the recombinant plant cell obtained in (a) to generate a transgenic plant.

15. The method of claim 14, further comprising (c) selecting a transgenic plant which is higher in height, or has a higher germination rate as compared with a plant of the same genetic background transformed with the wild type class C20 GA2ox while being grown under the same conditions.

16. The method of claim 14, further comprising (c) selecting a transgenic plant which has a height that is about 25% to 99%, 30% to 70%, or 40% to 60% of a non-transgenic plant of the same genetic background while being grown under the same conditions.

17. The method of claim 14, further comprising (c) selecting a transgenic plant exhibiting higher tiller numbers, earlier tillering, increased root system, lower shoot to root ratio, more efficient water consumption, higher chlorophyll content, higher mesophyll cell density, higher photosynthesis rate, higher grain yield, higher anti-oxidant activity, or higher tolerance to environmental stress, than a non-transgenic plant of the same genetic background while being grown under the same conditions.

18. The method of claim 17, wherein the environmental stress is selected from the group consisting of drought, temperature, salinity and oxidative stresses.

* * * * *

SEQUENCE LISTING

```
<160> NUMBER OF SEQ ID NOS: 84

<210> SEQ ID NO 1
<211> LENGTH: 358
<212> TYPE: PRT
<213> ORGANISM: Oryza sativa

<400> SEQUENCE: 1

Met Pro Ala Phe Ala Asp Ile Ala Ile Asp Pro Pro Leu Ala Asp Ser
1               5                   10                  15

Tyr Arg Ala Leu Ala Leu Leu Arg Arg Asp Arg Asp Gly Gly Ile Ala
            20                  25                  30
```

```
Pro Pro Ala Val Gln Met Val Gly Ser Gly Ala Val Leu Glu Arg
         35                  40                  45

Asp Leu Pro Met Val Asp Leu Glu Arg Leu Thr Arg Gly Gly Ala Gly
 50                  55                  60

Glu Arg Lys Ala Cys Ala Gly Ala Met Ala Arg Ala Ala Ser Glu Trp
 65                  70                  75                  80

Gly Phe Phe Gln Leu Thr Asn His Gly Val Gly Arg Glu Leu Met Glu
                 85                  90                  95

Glu Met Arg Arg Glu Gln Ala Arg Leu Phe Arg Leu Pro Phe Glu Thr
                100                 105                 110

Lys Glu Lys Ala Gly Leu Leu Asn Gly Ser Tyr Arg Trp Gly Asn Pro
            115                 120                 125

Thr Ala Thr Ser Leu Arg His Leu Ser Trp Ser Glu Ala Phe His Val
130                 135                 140

Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Ala Leu Ala Glu Glu Leu Thr Gly Arg Gly
            180                 185                 190

Gly Gly Gly Ala Ser Ala Ala Pro Trp Phe Pro Ala Gly Cys Asp Glu
        195                 200                 205

Thr Thr Cys Phe Leu Arg Leu Asn Arg Tyr Pro Ala Cys Pro Phe Ala
    210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
            260                 265                 270

Gly Asp Leu Phe Gln Ala Trp Ser Asn Asn Arg Tyr Lys Ser Val Glu
        275                 280                 285

His Lys Val Val Ala Asn Ala Lys Thr Asp Arg Leu Ser Val Ala Tyr
    290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Gly Lys Lys Ile Gly Leu Pro Asn Phe Phe
            340                 345                 350

Lys His Ser Ser Val Gln
        355

<210> SEQ ID NO 2
<211> LENGTH: 5
<212> TYPE: PRT
<213> ORGANISM: Oryza sativa
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Tyr Arg Trp Gly
 1               5
```

-continued

```
<210> SEQ ID NO 3
<211> LENGTH: 12
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 3

Xaa Xaa Ser Xaa Ser Glu Ala Xaa His Xaa Xaa Xaa
1               5                   10

<210> SEQ ID NO 4
<211> LENGTH: 14
<212> TYPE: PRT
<213> ORGANISM: Oryza sativa
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 4

Asp Val Xaa Xaa Xaa Gly Xaa Lys Xaa Gly Leu Xaa Xaa Phe
1               5                   10

<210> SEQ ID NO 5
<211> LENGTH: 5
<212> TYPE: PRT
<213> ORGANISM: Oryza sativa

<400> SEQUENCE: 5

Ser Tyr Arg Trp Gly
1               5

<210> SEQ ID NO 6
<211> LENGTH: 12
<212> TYPE: PRT
<213> ORGANISM: Oryza sativa

<400> SEQUENCE: 6

His Leu Ser Trp Ser Glu Ala Phe Arg Val Pro Leu
1               5                   10

<210> SEQ ID NO 7
<211> LENGTH: 14
<212> TYPE: PRT
```

<213> ORGANISM: Oryza sativa

<400> SEQUENCE: 7

```
Asp Val Arg Thr Thr Gly Lys Lys Ile Gly Leu Pro Asn Phe
1               5                   10
```

<210> SEQ ID NO 8
<211> LENGTH: 358
<212> TYPE: PRT
<213> ORGANISM: Oryza sativa

<400> SEQUENCE: 8

```
Met Pro Ala Phe Ala Asp Ile Ala Ile Asp Pro Pro Leu Ala Asp Ser
1               5                   10                  15

Tyr Arg Ala Leu Ala Leu Leu Arg Arg Asp Arg Asp Gly Gly Ile Ala
                20                  25                  30

Pro Pro Ala Val Gln Met Val Gly Ser Gly Gly Ala Val Leu Glu Arg
            35                  40                  45

Asp Leu Pro Met Val Asp Leu Glu Arg Leu Thr Arg Gly Gly Ala Gly
        50                  55                  60

Glu Arg Lys Ala Cys Ala Gly Ala Met Ala Arg Ala Ala Ser Glu Trp
65                  70                  75                  80

Gly Phe Phe Gln Leu Thr Asn His Gly Val Gly Arg Glu Leu Met Glu
                85                  90                  95

Glu Met Arg Arg Glu Gln Ala Arg Leu Phe Arg Leu Pro Phe Glu Thr
                100                 105                 110

Lys Glu Lys Ala Gly Leu Leu Asn Gly Ser Ala Arg Trp Gly Asn Pro
            115                 120                 125

Thr Ala Thr Ser Leu Arg His Leu Ser Trp Ser Glu Ala Phe His Val
        130                 135                 140

Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Ala Leu Ala Glu Glu Leu Thr Gly Arg Gly
                180                 185                 190

Gly Gly Gly Ala Ser Ala Ala Pro Trp Phe Pro Ala Gly Cys Asp Glu
            195                 200                 205

Thr Thr Cys Phe Leu Arg Leu Asn Arg Tyr Pro Ala Cys Pro Phe Ala
        210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
                260                 265                 270

Gly Asp Leu Phe Gln Ala Trp Ser Asn Asn Arg Tyr Lys Ser Val Glu
            275                 280                 285

His Lys Val Val Ala Asn Ala Lys Thr Asp Arg Leu Ser Val Ala Tyr
        290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Gly Lys Lys Ile Gly Leu Pro Asn Phe Phe
```

Lys His Ser Ser Val Gln
            355

<210> SEQ ID NO 9
<211> LENGTH: 358
<212> TYPE: PRT
<213> ORGANISM: Oryza sativa

<400> SEQUENCE: 9

Met Pro Ala Phe Ala Asp Ile Ala Ile Asp Pro Leu Ala Asp Ser
1               5                   10                  15

Tyr Arg Ala Leu Ala Leu Leu Arg Arg Asp Arg Asp Gly Gly Ile Ala
                20                  25                  30

Pro Pro Ala Val Gln Met Val Gly Ser Gly Gly Ala Val Leu Glu Arg
                35                  40                  45

Asp Leu Pro Met Val Asp Leu Glu Arg Leu Thr Arg Gly Gly Ala Gly
            50                  55                  60

Glu Arg Lys Ala Cys Ala Gly Ala Met Ala Arg Ala Ala Ser Glu Trp
65                  70                  75                  80

Gly Phe Phe Gln Leu Thr Asn His Gly Val Gly Arg Glu Leu Met Glu
                85                  90                  95

Glu Met Arg Arg Glu Gln Ala Arg Leu Phe Arg Leu Pro Phe Glu Thr
                100                 105                 110

Lys Glu Lys Ala Gly Leu Leu Asn Gly Ser Tyr Arg Trp Gly Asn Pro
            115                 120                 125

Thr Ala Thr Ser Leu Arg His Leu Ser Trp Ser Ala Ala Phe His Val
            130                 135                 140

Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Ala Leu Ala Glu Glu Leu Thr Gly Arg Gly
                180                 185                 190

Gly Gly Gly Ala Ser Ala Ala Pro Trp Phe Pro Ala Gly Cys Asp Glu
            195                 200                 205

Thr Thr Cys Phe Leu Arg Leu Asn Arg Tyr Pro Ala Cys Pro Phe Ala
210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
            260                 265                 270

Gly Asp Leu Phe Gln Ala Trp Ser Asn Asn Arg Tyr Lys Ser Val Glu
            275                 280                 285

His Lys Val Val Ala Asn Ala Lys Thr Asp Arg Leu Ser Val Ala Tyr
            290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Gly Lys Lys Ile Gly Leu Pro Asn Phe Phe
            340                 345                 350

Lys His Ser Ser Val Gln
        355

<210> SEQ ID NO 10
<211> LENGTH: 358
<212> TYPE: PRT
<213> ORGANISM: Oryza sativa

<400> SEQUENCE: 10

Met Pro Ala Phe Ala Asp Ile Ala Ile Asp Pro Pro Leu Ala Asp Ser
1               5                   10                  15

Tyr Arg Ala Leu Ala Leu Leu Arg Arg Asp Arg Asp Gly Gly Ile Ala
                20                  25                  30

Pro Pro Ala Val Gln Met Val Gly Ser Gly Gly Ala Val Leu Glu Arg
            35                  40                  45

Asp Leu Pro Met Val Asp Leu Glu Arg Leu Thr Arg Gly Gly Ala Gly
        50                  55                  60

Glu Arg Lys Ala Cys Ala Gly Ala Met Ala Arg Ala Ala Ser Glu Trp
65                  70                  75                  80

Gly Phe Phe Gln Leu Thr Asn His Gly Val Gly Arg Glu Leu Met Glu
                85                  90                  95

Glu Met Arg Arg Glu Gln Ala Arg Leu Phe Arg Leu Pro Phe Glu Thr
                100                 105                 110

Lys Glu Lys Ala Gly Leu Leu Asn Gly Ser Tyr Arg Trp Gly Asn Pro
            115                 120                 125

Thr Ala Thr Ser Leu Arg His Leu Ser Trp Ser Glu Glu Phe His Val
        130                 135                 140

Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Ala Leu Ala Glu Glu Leu Thr Gly Arg Gly
                180                 185                 190

Gly Gly Gly Ala Ser Ala Ala Pro Trp Phe Pro Ala Gly Cys Asp Glu
            195                 200                 205

Thr Thr Cys Phe Leu Arg Leu Asn Arg Tyr Pro Ala Cys Pro Phe Ala
        210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
                260                 265                 270

Gly Asp Leu Phe Gln Ala Trp Ser Asn Asn Arg Tyr Lys Ser Val Glu
            275                 280                 285

His Lys Val Val Ala Asn Ala Lys Thr Asp Arg Leu Ser Val Ala Tyr
        290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Gly Lys Lys Ile Gly Leu Pro Asn Phe Phe
                340                 345                 350

Lys His Ser Ser Val Gln
        355

<210> SEQ ID NO 11
<211> LENGTH: 358
<212> TYPE: PRT
<213> ORGANISM: Oryza sativa

<400> SEQUENCE: 11

Met Pro Ala Phe Ala Asp Ile Ala Ile Asp Pro Pro Leu Ala Asp Ser
1               5                   10                  15

Tyr Arg Ala Leu Ala Leu Leu Arg Arg Asp Arg Asp Gly Gly Ile Ala
            20                  25                  30

Pro Pro Ala Val Gln Met Val Gly Ser Gly Gly Ala Val Leu Glu Arg
        35                  40                  45

Asp Leu Pro Met Val Asp Leu Glu Arg Leu Thr Arg Gly Gly Ala Gly
    50                  55                  60

Glu Arg Lys Ala Cys Ala Gly Ala Met Ala Arg Ala Ala Ser Glu Trp
65                  70                  75                  80

Gly Phe Phe Gln Leu Thr Asn His Gly Val Gly Arg Glu Leu Met Glu
                85                  90                  95

Glu Met Arg Arg Glu Gln Ala Arg Leu Phe Arg Leu Pro Phe Glu Thr
            100                 105                 110

Lys Glu Lys Ala Gly Leu Leu Asn Gly Ser Tyr Arg Trp Gly Asn Pro
        115                 120                 125

Thr Ala Thr Ser Leu Arg His Leu Ser Trp Ser Glu Ala Phe Ala Val
130                 135                 140

Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Ala Leu Ala Glu Glu Leu Thr Gly Arg Gly
            180                 185                 190

Gly Gly Gly Ala Ser Ala Ala Pro Trp Phe Pro Ala Gly Cys Asp Glu
        195                 200                 205

Thr Thr Cys Phe Leu Arg Leu Asn Arg Tyr Pro Ala Cys Pro Phe Ala
    210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
            260                 265                 270

Gly Asp Leu Phe Gln Ala Trp Ser Asn Asn Arg Tyr Lys Ser Val Glu
        275                 280                 285

His Lys Val Val Ala Asn Ala Lys Thr Asp Arg Leu Ser Val Ala Tyr
    290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Gly Lys Lys Ile Gly Leu Pro Asn Phe Phe
            340                 345                 350

Lys His Ser Ser Val Gln
        355

<210> SEQ ID NO 12
<211> LENGTH: 358
<212> TYPE: PRT
<213> ORGANISM: Oryza sativa

<400> SEQUENCE: 12

```
Met Pro Ala Phe Ala Asp Ile Ala Ile Asp Pro Pro Leu Ala Asp Ser
1               5                   10                  15

Tyr Arg Ala Leu Ala Leu Leu Arg Arg Asp Arg Asp Gly Gly Ile Ala
            20                  25                  30

Pro Pro Ala Val Gln Met Val Gly Ser Gly Gly Ala Val Leu Glu Arg
        35                  40                  45

Asp Leu Pro Met Val Asp Leu Glu Arg Leu Thr Arg Gly Gly Ala Gly
    50                  55                  60

Glu Arg Lys Ala Cys Ala Gly Ala Met Ala Arg Ala Ala Ser Glu Trp
65                  70                  75                  80

Gly Phe Phe Gln Leu Thr Asn His Gly Val Gly Arg Glu Leu Met Glu
                85                  90                  95

Glu Met Arg Arg Glu Gln Ala Arg Leu Phe Arg Leu Pro Phe Glu Thr
            100                 105                 110

Lys Glu Lys Ala Gly Leu Leu Asn Gly Ser Tyr Arg Trp Gly Asn Pro
        115                 120                 125

Thr Ala Thr Ser Leu Arg His Leu Ser Trp Ser Glu Ala Phe His Val
    130                 135                 140

Pro Leu Ala Ser Ile Ser Gly Ala Asp Cys Asp Phe Gly Asp Leu Thr
145                 150                 155                 160

Ser Leu Arg Gly Val Met Gln Glu Val Ala Glu Ala Met Ser Arg Val
                165                 170                 175

Ala Asn Thr Val Ala Ala Ala Leu Ala Glu Glu Leu Thr Gly Arg Gly
            180                 185                 190

Gly Gly Gly Ala Ser Ala Ala Pro Trp Phe Pro Ala Gly Cys Asp Glu
        195                 200                 205

Thr Thr Cys Phe Leu Arg Leu Asn Arg Tyr Pro Ala Cys Pro Phe Ala
    210                 215                 220

Ala Asp Thr Phe Gly Leu Val Pro His Thr Asp Ser Asp Phe Leu Thr
225                 230                 235                 240

Val Leu Cys Gln Asp Gln Val Gly Gly Leu His Leu Met Lys Asp Ser
                245                 250                 255

Arg Trp Val Ala Val Arg Pro Arg Pro Asp Ala Leu Val Val Asn Ile
            260                 265                 270

Gly Asp Leu Phe Gln Ala Trp Ser Asn Asn Arg Tyr Lys Ser Val Glu
        275                 280                 285

His Lys Val Val Ala Asn Ala Lys Thr Asp Arg Leu Ser Val Ala Tyr
    290                 295                 300

Phe Leu Cys Pro Ser Tyr Asp Ser Leu Val Gly Thr Cys Gly Glu Pro
305                 310                 315                 320

Ser Pro Tyr Arg Ala Phe Thr Phe Gly Glu Tyr Arg Lys Lys Val Gln
                325                 330                 335

Glu Asp Val Arg Thr Thr Ala Lys Lys Ile Gly Leu Pro Asn Phe Phe
            340                 345                 350

Lys His Ser Ser Val Gln
        355
```

<210> SEQ ID NO 13
<211> LENGTH: 1077

```
<212> TYPE: DNA
<213> ORGANISM: Oryza sativa

<400> SEQUENCE: 13
atgccggcct tcgccgacat cgccatcgac ccgcctctgg ccgacagcta ccgcgcgctg     60
gcgctgctcc gccgcgaccg cgacggtggc attgcgccgc cggctgtgca gatggtcggc    120
tcgggcggcg ccgtgctgga gcgcgacctg ccgatggtgg acctggagcg gctgacgagg    180
ggcggcgcgg gggagaggaa ggcgtgcgcg ggcgccatgg cgagggcggc gtcggagtgg    240
gggttcttcc agctgaccaa ccacggcgtg gccgggagc tgatggagga gatgaggcgg     300
gagcaggcaa ggctgttccg tctgccgttc gaaaccaagg agaaggccgg cctgctcaac    360
ggctcggctc ggtggggcaa ccccaccgcc acgtcgctcc gccacctctc gtggtcggag    420
gcgttccacg tcccgctcgc cagcatctcc ggggcggatt gcgactttgg agacctcacc    480
tccttaaggg gcgtgatgca ggaggtggcc gaagcgatgt cgcgggtggc gaacacggtg    540
gcagcggcgc tggcggagga gctgaccggg cgcggaggcg gcggggcatc ggcggcgccg    600
tggttccctg cggggtgcga cgagacgacg tgcttcctgc ggctcaaccg gtacccggcg    660
tgccctttcg cggcggacac gttcgggctg gtgccgcaca cggacagcga ctttctcacc    720
gtcctgtgcc aggaccaggt cgggggcctg cacctgatga aggactcccg gtgggtggcc    780
gtcaggccac gccccgacgc cctcgtcgtc aacatcggcg atctgtttca ggcgtggagc    840
aacaacaggt acaagagcgt ggagcataaa gtggtggcca acgccaagac ggaccggcta    900
tcggtggcct acttcctgtg cccgtcctac gactcgcttg tcgggacatg cggcgagcca    960
tcgccataca gggccttcac cttcggggag tacaggaaga aggtgcagga agacgtcagg   1020
acaaccggga aaaagattgg cctcccaaac tttttcaagc attcttcagt acaataa      1077

<210> SEQ ID NO 14
<211> LENGTH: 1077
<212> TYPE: DNA
<213> ORGANISM: Oryza sativa

<400> SEQUENCE: 14
atgccggcct tcgccgacat cgccatcgac ccgcctctgg ccgacagcta ccgcgcgctg     60
gcgctgctcc gccgcgaccg cgacggtggc attgcgccgc cggctgtgca gatggtcggc    120
tcgggcggcg ccgtgctgga gcgcgacctg ccgatggtgg acctggagcg gctgacgagg    180
ggcggcgcgg gggagaggaa ggcgtgcgcg ggcgccatgg cgagggcggc gtcggagtgg    240
gggttcttcc agctgaccaa ccacggcgtg gccgggagc tgatggagga gatgaggcgg     300
gagcaggcaa ggctgttccg tctgccgttc gaaaccaagg agaaggccgg cctgctcaac    360
ggctcgtacc ggtggggcaa ccccaccgcc acgtcgctcc gccacctctc gtggtcggct    420
gcgttccacg tcccgctcgc cagcatctcc ggggcggatt gcgactttgg agacctcacc    480
tccttaaggg gcgtgatgca ggaggtggcc gaagcgatgt cgcgggtggc gaacacggtg    540
gcagcggcgc tggcggagga gctgaccggg cgcggaggcg gcggggcatc ggcggcgccg    600
tggttccctg cggggtgcga cgagacgacg tgcttcctgc ggctcaaccg gtacccggcg    660
tgccctttcg cggcggacac gttcgggctg gtgccgcaca cggacagcga ctttctcacc    720
gtcctgtgcc aggaccaggt cgggggcctg cacctgatga aggactcccg gtgggtggcc    780
gtcaggccac gccccgacgc cctcgtcgtc aacatcggcg atctgtttca ggcgtggagc    840
aacaacaggt acaagagcgt ggagcataaa gtggtggcca acgccaagac ggaccggcta    900
```

```
tcggtggcct acttcctgtg cccgtcctac gactcgcttg tcgggacatg cggcgagcca    960
tcgccataca gggccttcac cttcggggag tacaggaaga aggtgcagga agacgtcagg   1020
acaaccggga aaagattgg cctcccaaac tttttcaagc attcttcagt acaataa      1077
```

<210> SEQ ID NO 15
<211> LENGTH: 1077
<212> TYPE: DNA
<213> ORGANISM: Oryza sativa

<400> SEQUENCE: 15

```
atgccggcct tcgccgacat cgccatcgac ccgcctctgg ccgacagcta ccgcgcgctg     60
gcgctgctcc gccgcgaccg cgacggtggc attgcgccgc cggctgtgca gatggtcggc    120
tcgggcggcg ccgtgctgga gcgcgacctg ccgatggtgg acctggagcg gctgacgagg    180
ggcggcgcgg gggagaggaa ggcgtgcgcg ggcgccatgg cgagggcggc gtcggagtgg    240
gggttcttcc agctgaccaa ccacggcgtg gccgggagc tgatggagga gatgaggcgg     300
gagcaggcaa ggctgttccg tctgccgttc gaaaccaagg agaaggccgg cctgctcaac    360
ggctcgtacc ggtggggcaa ccccaccgcc acgtcgctcc gccacctctc gtggtcggag    420
gagttccacg tcccgctcgc cagcatctcc ggggcggatt gcgactttgg agacctcacc    480
tccttaaggg gcgtgatgca ggaggtggcc gaagcgatgt cgcgggtggc gaacacggtg    540
gcagcggcgc tggcggagga gctgaccggg cgcgaggcg gcgggcatc ggcggcgccg      600
tggttccctg cggggtgcga cgagacgacg tgcttcctgc ggctcaaccg gtacccggcg    660
tgccctttcg cggcggacac gttcgggctg gtgccgcaca cggacagcga ctttctcacc    720
gtcctgtgcc aggaccaggt cggggggcctg cacctgatga aggactcccg gtgggtggcc    780
gtcaggccac gccccgacgc cctcgtcgtc aacatcggcg atctgtttca ggcgtggagc    840
aacaacaggt acaagagcgt ggagcataaa gtggtggcca acgccaagac ggaccggcta    900
tcggtggcct acttcctgtg cccgtcctac gactcgcttg tcgggacatg cggcgagcca    960
tcgccataca gggccttcac cttcggggag tacaggaaga aggtgcagga agacgtcagg   1020
acaaccggga aaagattgg cctcccaaac tttttcaagc attcttcagt acaataa      1077
```

<210> SEQ ID NO 16
<211> LENGTH: 1077
<212> TYPE: DNA
<213> ORGANISM: Oryza sativa

<400> SEQUENCE: 16

```
atgccggcct tcgccgacat cgccatcgac ccgcctctgg ccgacagcta ccgcgcgctg     60
gcgctgctcc gccgcgaccg cgacggtggc attgcgccgc cggctgtgca gatggtcggc    120
tcgggcggcg ccgtgctgga gcgcgacctg ccgatggtgg acctggagcg gctgacgagg    180
ggcggcgcgg gggagaggaa ggcgtgcgcg ggcgccatgg cgagggcggc gtcggagtgg    240
gggttcttcc agctgaccaa ccacggcgtg gccgggagc tgatggagga gatgaggcgg     300
gagcaggcaa ggctgttccg tctgccgttc gaaaccaagg agaaggccgg cctgctcaac    360
ggctcgtacc ggtggggcaa ccccaccgcc acgtcgctcc gccacctctc gtggtcggag    420
gcgttcgccg tcccgctcgc cagcatctcc ggggcggatt gcgactttgg agacctcacc    480
tccttaaggg gcgtgatgca ggaggtggcc gaagcgatgt cgcgggtggc gaacacggtg    540
gcagcggcgc tggcggagga gctgaccggg cgcgaggcg gcgggcatc ggcggcgccg      600
tggttccctg cggggtgcga cgagacgacg tgcttcctgc ggctcaaccg gtacccggcg    660
```

```
tgcccttcg cggcggacac gttcgggctg gtgccgcaca cggacagcga ctttctcacc      720
gtcctgtgcc aggaccaggt cggggggcctg cacctgatga aggactcccg gtgggtggcc    780
gtcaggccac gccccgacgc cctcgtcgtc aacatcggcg atctgtttca ggcgtggagc    840
aacaacaggt acaagagcgt ggagcataaa gtggtggcca acgccaagac ggaccggcta    900
tcggtggcct acttcctgtg cccgtcctac gactcgcttg tcgggacatg cggcgagcca    960
tcgccataca gggccttcac cttcggggag tacaggaaga aggtgcagga agacgtcagg   1020
acaaccggga aaaagattgg cctcccaaac ttttttcaagc attcttcagt acaataa      1077
```

<210> SEQ ID NO 17
<211> LENGTH: 1077
<212> TYPE: DNA
<213> ORGANISM: Oryza sativa

<400> SEQUENCE: 17

```
atgccggcct tcgccgacat cgccatcgac ccgcctctgg ccgacagcta ccgcgcgctg     60
gcgctgctcc gccgcgaccg cgacggtggc attgcgccgc cggctgtgca gatggtcggc    120
tcgggcggcg ccgtgctgga gcgcgacctg ccgatggtgg acctgagcg gctgacgagg    180 ggcggcgcgg gggagaggaa ggcgtgcgcg gccgccatgg cgaggggcgg gtcggagtgg    240
gggttcttcc agctgaccaa ccacggcgtg gccgggagc tgatggagga gatgaggcgg    300
gagcaggcaa ggctgttccg tctgccgttc gaaaccaagg agaaggccgg cctgctcaac    360
ggctcgtacc ggtggggcaa ccccaccgcc acgtcgctcc gccacctctc gtggtcggag    420
gcgttccacg tcccgctcgc cagcatctcc ggggcggatt gcgactttgg agacctcacc    480
tccttaaggg gcgtgatgca ggaggtggcc gaagcgatgt cgcgggtggc gaacacggtg    540
gcagcggcgc tggcggagga gctgaccggg cgcggaggcg gcggggcatc ggcggcgccg    600
tggttccctg cggggtgcga cgagacgacg tgcttcctgc ggctcaaccg gtacccggcg    660 tgcccttcg cggcggacac gttcgggctg gtgccgcaca cggacagcga ctttctcacc    720
gtcctgtgcc aggaccaggt cggggggcctg cacctgatga aggactcccg gtgggtggcc    780
gtcaggccac gccccgacgc cctcgtcgtc aacatcggcg atctgtttca ggcgtggagc    840
aacaacaggt acaagagcgt ggagcataaa gtggtggcca acgccaagac ggaccggcta    900
tcggtggcct acttcctgtg cccgtcctac gactcgcttg tcgggacatg cggcgagcca    960
tcgccataca gggccttcac cttcggggag tacaggaaga aggtgcagga agacgtcagg   1020
acaaccgcca aaaagattgg cctcccaaac ttttttcaagc attcttcagt acaataa      1077
```

<210> SEQ ID NO 18
<211> LENGTH: 336
<212> TYPE: PRT
<213> ORGANISM: Oryza sativa

<400> SEQUENCE: 18

```
Met Ala Ser Gln Pro Pro Phe Lys Thr Asn Phe Cys Ser Ile Phe Gly
1               5                   10                  15

Ser Ser Phe Pro Asn Ser Thr Ser Glu Ser Asn Thr Asn Thr Ser Thr
            20                  25                  30

Ile Gln Thr Ser Gly Ile Lys Leu Pro Val Ile Asp Leu Ser His Leu
        35                  40                  45

Thr Ser Gly Glu Glu Val Lys Arg Lys Arg Cys Val Lys Gln Met Val
    50                  55                  60
```

```
Ala Ala Ala Lys Glu Trp Gly Phe Phe Gln Ile Val Asn His Gly Ile
 65                  70                  75                  80

Pro Lys Asp Val Phe Glu Met Met Leu Leu Glu Glu Lys Lys Leu Phe
             85                  90                  95

Asp Gln Pro Phe Ser Val Lys Val Arg Glu Arg Phe Ser Asp Leu Ser
            100                 105                 110

Lys Asn Ser Tyr Arg Trp Gly Asn Pro Ser Ala Thr Ser Pro Ala Gln
        115                 120                 125

Tyr Ser Val Ser Glu Ala Phe His Ile Ile Leu Ser Glu Val Ser Arg
    130                 135                 140

Ile Ser Asp Asp Arg Asn Asn Leu Arg Thr Ile Val Glu Thr Tyr Val
145                 150                 155                 160

Gln Glu Ile Ala Arg Val Ala Gln Met Ile Cys Glu Ile Leu Gly Lys
                165                 170                 175

Gln Val Asn Val Ser Ser Glu Tyr Phe Glu Asn Ile Phe Glu Leu Glu
            180                 185                 190

Asn Ser Phe Leu Arg Leu Asn Lys Tyr His Pro Ser Val Phe Gly Ser
        195                 200                 205

Glu Val Phe Gly Leu Val Pro His Thr Asp Thr Ser Phe Leu Thr Ile
    210                 215                 220

Leu Ser Gln Asp Gln Ile Gly Gly Leu Glu Leu Glu Asn Asn Gly Gln
225                 230                 235                 240

Trp Ile Ser Val Lys Pro Cys Leu Glu Ala Leu Thr Val Asn Ile Gly
                245                 250                 255

Asp Met Phe Gln Ala Leu Ser Asn Gly Val Tyr Gln Ser Val Arg His
            260                 265                 270

Arg Val Ile Ser Pro Ala Asn Ile Glu Arg Met Ser Ile Ala Phe Phe
        275                 280                 285

Val Cys Pro Tyr Leu Glu Thr Glu Ile Asp Cys Phe Gly Tyr Pro Lys
    290                 295                 300

Lys Tyr Arg Arg Phe Ser Phe Arg Glu Tyr Lys Glu Gln Ser Glu His
305                 310                 315                 320

Asp Val Lys Glu Thr Gly Asp Lys Val Gly Leu Ser Arg Phe Leu Ile
                325                 330                 335

<210> SEQ ID NO 19
<211> LENGTH: 293
<212> TYPE: PRT
<213> ORGANISM: Oryza sativa

<400> SEQUENCE: 19

Met Asp Pro Pro Phe Asn Glu Ile Tyr Asn Asn Leu Leu Tyr Asn Gln
  1               5                  10                  15

Ile Thr Lys Lys Asp Asn Asp Val Ser Glu Ile Pro Phe Ser Phe Ser
             20                  25                  30

Val Thr Ala Val Val Glu Glu Val Glu Leu Pro Val Ile Asp Val Ser
             35                  40                  45

Arg Leu Ile Asp Gly Ala Glu Glu Arg Glu Lys Cys Lys Glu Ala
    50                  55                  60

Ile Ala Arg Ala Ser Arg Glu Trp Gly Phe Phe Gln Val Ile Asn His
 65                  70                  75                  80

Gly Ile Ser Met Asp Val Leu Glu Lys Met Arg Gln Glu Gln Ile Arg
                 85                  90                  95

Val Phe Arg Glu Pro Phe Asp Lys Lys Ser Asn Ser Thr Met Glu Lys
            100                 105                 110
```

```
Phe Ala Ser Glu Ser Glu Ala Leu Ala Tyr Met Leu Ala Glu Val Leu
            115                 120                 125

Ala Glu Lys Ser Gly Gln Asn Ser Ser Phe Phe Lys Glu Asn Cys Val
130                 135                 140

Arg Asn Thr Cys Tyr Leu Arg Met Asn Arg Tyr Pro Pro Cys Pro Lys
145                 150                 155                 160

Pro Ser Glu Val Tyr Gly Leu Met Pro His Thr Asp Ser Asp Phe Leu
                165                 170                 175

Thr Ile Leu Tyr Gln Asp Gln Val Gly Gly Leu Gln Leu Ile Lys Asp
            180                 185                 190

Asn Arg Trp Ile Ala Val Lys Pro Asn Pro Lys Ala Leu Ile Ile Asn
            195                 200                 205

Ile Gly Asp Leu Phe Gln Ala Trp Ser Asn Gly Met Tyr Lys Ser Val
210                 215                 220

Glu His Arg Val Met Thr Asn Pro Lys Val Glu Arg Phe Ser Thr Ala
225                 230                 235                 240

Tyr Phe Met Cys Pro Ser Tyr Asp Ala Val Ile Glu Cys Ser Ser Asp
                245                 250                 255

Arg Pro Ala Tyr Arg Asn Phe Ser Phe Arg Glu Phe Arg Gln Gln Val
                260                 265                 270

Gln Glu Asp Val Lys Lys Phe Gly Phe Lys Val Gly Leu Pro Arg Phe
275                 280                 285

Leu Asn His Val Tyr
            290

<210> SEQ ID NO 20
<211> LENGTH: 374
<212> TYPE: PRT
<213> ORGANISM: Oryza sativa

<400> SEQUENCE: 20

Met Ala Ser Thr Lys Val Val Glu His Leu Lys Glu Asn Val Leu Trp
1               5                   10                  15

Lys Gln Ala Ile Met Asp Arg Asn Ala Asn Ile Ser Asp Pro Pro Phe
            20                  25                  30

Glu Glu Thr Tyr Lys Asn Leu Leu Lys His Asn Ile Thr Pro Leu
            35                  40                  45

Thr Thr Thr Thr Thr Thr Thr Thr Thr Ala Thr Ile Glu Val Arg
        50                  55                  60

Asp Leu Pro Leu Ile Asp Leu Ser Arg Leu Val Ala Thr Ala Ala Lys
65                  70                  75                  80

Glu Arg Glu Asn Cys Lys Arg Asp Ile Ala Asn Ala Ser Arg Glu Trp
                85                  90                  95

Gly Phe Phe Gln Val Val Asn His Gly Ile Pro His Arg Met Leu Glu
            100                 105                 110

Glu Met Asn Lys Glu Gln Val Lys Val Phe Arg Glu Pro Phe Asn Lys
            115                 120                 125

Lys Lys Gly Asp Asn Cys Met Asn Leu Arg Leu Ser Pro Gly Ser Tyr
130                 135                 140

Arg Trp Gly Ser Pro Thr Pro Asn Cys Leu Ser Gln Leu Ser Trp Ser
145                 150                 155                 160

Glu Ala Phe His Ile Pro Met Asn Asp Ile Cys Ser Asn Ala Pro Arg
                165                 170                 175

Asn Ile Ala Asn Gly Asn Pro Asn Ile Ser Asn Leu Cys Ser Thr Val
```

```
            180                 185                 190
Lys Gln Phe Ala Thr Thr Val Ser Glu Leu Ala Asn Lys Leu Ala Asn
            195                 200                 205
Ile Leu Val Glu Lys Leu Gly His Asp Glu Leu Thr Phe Ile Glu Glu
            210                 215                 220
Lys Cys Ser Pro Asn Thr Cys Tyr Leu Arg Met Asn Arg Tyr Pro Pro
225                 230                 235                 240
Cys Pro Lys Tyr Ser His Val Leu Gly Leu Met Pro His Thr Asp Ser
            245                 250                 255
Asp Phe Leu Thr Ile Leu Tyr Gln Asp Gln Val Gly Gly Leu Gln Leu
            260                 265                 270
Val Lys Asp Gly Arg Trp Ile Ser Val Lys Pro Asn Pro Glu Ala Leu
            275                 280                 285
Ile Val Asn Ile Gly Asp Leu Phe Gln Ala Trp Ser Asn Gly Val Tyr
            290                 295                 300
Lys Ser Val Val His Arg Val Val Ala Asn Pro Arg Phe Glu Arg Phe
305                 310                 315                 320
Ser Thr Ala Tyr Phe Leu Cys Pro Ser Gly Asp Ala Val Ile Gln Ser
            325                 330                 335
Tyr Arg Glu Pro Ser Met Tyr Arg Lys Phe Ser Phe Gly Glu Tyr Arg
            340                 345                 350
Gln Gln Val Gln Gln Asp Val Arg Glu Phe Gly His Lys Ile Gly Leu
            355                 360                 365
Ser Arg Phe Leu Ile Cys
    370

<210> SEQ ID NO 21
<211> LENGTH: 341
<212> TYPE: PRT
<213> ORGANISM: Oryza sativa

<400> SEQUENCE: 21

Met Glu Glu His Asp Tyr Asp Ser Asn Ser Asn Pro Pro Leu Met Ser
1               5                   10                  15
Thr Tyr Lys His Leu Phe Val Glu Gln His Arg Leu Asp Met Asp Met
            20                  25                  30
Gly Ala Ile Asp Val Asp Glu Cys Glu Leu Pro Val Ile Asp Leu Ala
            35                  40                  45
Gly Leu Met Glu Ala Glu Gln Val Cys Arg Ala Asp Met Val Arg Ala
        50                  55                  60
Ala Ser Glu Trp Gly Phe Phe Gln Val Thr Asn His Gly Val Pro Gln
65                  70                  75                  80
Ala Leu Leu Arg Glu Leu His Asp Ala Gln Val Ala Val Phe Arg Arg
            85                  90                  95
Pro Phe Gln Glu Lys Val Thr Glu Arg Leu Leu Gly Phe Ser Pro Glu
            100                 105                 110
Ser Tyr Arg Trp Gly Thr Pro Thr Ala Lys Cys Leu Glu Gln Leu Ser
            115                 120                 125
Trp Ser Glu Ala Tyr His Ile Pro Met Thr Thr Pro Arg Pro Ser Thr
            130                 135                 140
Ser Ile Arg Ala Arg Ala Val Ile Glu Glu Val Ser Arg Ala Met Tyr
145                 150                 155                 160
Glu Leu Ala Gln Lys Leu Ala Glu Ile Leu Met Arg Gly Leu Pro Gly
            165                 170                 175
```

Ala Gly Glu Gly Glu Thr Met Val Thr Thr Arg Glu Thr Cys Phe
            180                 185                 190

Leu Arg Leu Asn Arg Tyr Pro Pro Cys Ala Met Ala Met Gly Gly Phe
        195                 200                 205

Gly Leu Cys Pro His Thr Asp Ser Asp Leu Leu Thr Ile Val His Gln
    210                 215                 220

Gln Gln Asp Thr Val Gly Gly Leu Gln Leu Leu Lys Gly Gly Arg Trp
225                 230                 235                 240

Val Ala Val Lys Pro Ser Pro Ser Thr Leu Ile Val Asn Val Gly Asp
                245                 250                 255

Leu Leu Gln Ala Trp Ser Asn Asp Val Tyr Lys Ser Val Glu His Arg
        260                 265                 270

Val Met Ala Asn Ala Thr Leu Glu Arg Phe Ser Met Ala Phe Phe Leu
    275                 280                 285

Cys Pro Ser Tyr His Thr Leu Ile Ile Pro Ser Ser Ser His Val His
    290                 295                 300

Asp Asp Asp Ala His Tyr Arg Ser Phe Thr Phe Gly Glu Tyr Arg Lys
305                 310                 315                 320

Gln Ile Met Glu Asp Val Arg Ser Thr Gly Arg Lys Ile Gly Leu His
                325                 330                 335

Arg Phe Arg Thr Arg
            340

<210> SEQ ID NO 22
<211> LENGTH: 359
<212> TYPE: PRT
<213> ORGANISM: Oryza sativa

<400> SEQUENCE: 22

Met Pro Ala Ile Ala Asp Cys Ala Ala Asp Pro Leu Ala Asp Ser
1               5                   10                  15

Tyr Tyr Thr Leu Leu Arg Leu Gly Gly Asp Asp Asp Asp Ala Cys
            20                  25                  30

Thr Lys Val Thr Thr Thr Pro Gln Pro Val Ser Glu Cys Glu Leu Pro
            35                  40                  45

Met Ile Asp Val Gly Cys Leu Thr Ala Pro Thr Gly Ala Ala Ala
    50                  55                  60

Ala Ala Val Gly Gln Gln His Gln Ala Glu Glu Arg Ala Ala Cys Ala
65                  70                  75                  80

Ala Ala Ile Ala Ala Ala Ala Glu Trp Gly Phe Phe Gln Val Val
            85                  90                  95

Asn His Gly Val Ala Gln Glu Leu Leu Glu Ala Met Arg Arg Glu Gln
            100                 105                 110

Ala Arg Leu Phe Arg Leu Pro Phe Glu Ala Lys Ser Ser Ala Gly Leu
        115                 120                 125

Leu Asn Asp Ser Tyr Arg Trp Gly Thr Pro Thr Ala Thr Ser Leu Arg
130                 135                 140

Gln Leu Ser Trp Ser Glu Ala Phe His Leu Pro Leu Ala Gly Ile Ser
145                 150                 155                 160

Gly Lys Ser Cys Asn Tyr Gly Asp Leu Thr Ser Leu Arg Asp Val Thr
                165                 170                 175

Arg Glu Val Ala Asp Ala Met Ser Arg Leu Arg Ala Leu Ala Arg
            180                 185                 190

Val Leu Ala Glu Ser Leu Leu Gly His Ala Ala Gly Glu Arg Phe Pro
        195                 200                 205

```
        Glu Gly Cys Asp Asp Ala Thr Cys Phe Leu Arg Leu Asn Arg Tyr Pro
            210                 215                 220

Pro Cys Pro Phe Pro Pro Asp Asp Ala Phe Gly Leu Val Pro His Thr
        225                 230                 235                 240

Asp Ser Asp Phe Leu Thr Val Leu Cys Gln Asp His Val Gly Gly Leu
                        245                 250                 255

Gln Leu Met Lys Gly Ser Arg Trp Val Ala Val Lys Pro Ile Pro Gly
                    260                 265                 270

Ala Leu Ile Val Asn Ile Gly Asp Leu Phe Gln Ala Trp Ser Asn Asn
                275                 280                 285

Arg Tyr Lys Ser Val Glu His Arg Val Met Thr Asn Ala Thr Thr Glu
            290                 295                 300

Arg Tyr Ser Val Ala Tyr Phe Leu Cys Pro Ser Tyr Asp Ser Pro Ile
        305                 310                 315                 320

Gly Thr Cys Arg Glu Pro Ser Pro Tyr Lys Ala Phe Thr Phe Gly Glu
                        325                 330                 335

Tyr Arg Arg Arg Val Gln Glu Asp Val Lys Lys Thr Gly Lys Lys Thr
                    340                 345                 350

Gly Leu Ser Asn Phe Leu Val
                355

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
ctcaacggct cggctcggtg gggcaac                                        27

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
gttgccccac cgagccgagc cgttgag                                        27

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
cgtcgctcgc tcacctctcg tggtc                                          25

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
gaccacgaga ggtgagcgag cgacg                                          25
```

```
<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
ccacctctcg gcttcggagg cgttc                                       25

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
gaacgcctcc gaagccgaga ggtgg                                       25

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
ctctcgtggt cggctgcgtt ccacgtc                                     27

<210> SEQ ID NO 30
<211> LENGTH: 27
<212> TYPE: DNA
<213> ORGANISM: Artificial Sequence
<220> FEATURE:
<223> OTHER INFORMATION: primer

<400> SEQUENCE: 30
gacgtggaac gcagccgacc acgagag                                     27

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
cgtggtcgga ggagttccac gtccc                                       25

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
gggacgtgga actcctccga ccacg                                       25

<210> SEQ ID NO 33
<211> LENGTH: 26
<212> TYPE: DNA
<213> ORGANISM: Artificial Sequence
<220> FEATURE:
<223> OTHER INFORMATION: primer
```

<400> SEQUENCE: 33
gtcggaggcg ttcgccgtcc cgctcg                                               26

<210> SEQ ID NO 34
<211> LENGTH: 26
<212> TYPE: DNA
<213> ORGANISM: Artificial Sequence
<220> FEATURE:
<223> OTHER INFORMATION: primer

<400> SEQUENCE: 34
cgagcgggac ggcgaacgcc tccgac                                               26

<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
gaaggtgcag gaagccgtca ggacaac                                              27

<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36
gttgtcctga cggcttcctg caccttc                                              27

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
gtgcaggaag acgccaggac aaccg                                                25

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
cggttgtcct ggcgtcttcc tgcac                                                25

<210> SEQ ID NO 39
<211> LENGTH: 27
<212> TYPE: DNA
<213> ORGANISM: Artificial Sequence
<220> FEATURE:
<223> OTHER INFORMATION: primer

<400> SEQUENCE: 39
gaagacgtca gggcaaccgg gaaaaag                                              27

<210> SEQ ID NO 40

```
<211> LENGTH: 27
<212> TYPE: DNA
<213> ORGANISM: Artificial Sequence
<220> FEATURE:
<223> OTHER INFORMATION: primer

<400> SEQUENCE: 40
cttttccccg gttgccctga cgtcttc                                          27

<210> SEQ ID NO 41
<211> LENGTH: 27
<212> TYPE: DNA
<213> ORGANISM: Artificial Sequence
<220> FEATURE:
<223> OTHER INFORMATION: primer

<400> SEQUENCE: 41
gaagacgtca ggacagccgg gaaaaag                                          27

<210> SEQ ID NO 42
<211> LENGTH: 27
<212> TYPE: DNA
<213> ORGANISM: Artificial Sequence
<220> FEATURE:
<223> OTHER INFORMATION: primer

<400> SEQUENCE: 42
cttttccccg gctgtcctga cgtcttc                                          27

<210> SEQ ID NO 43
<211> LENGTH: 28
<212> TYPE: DNA
<213> ORGANISM: Artificial Sequence
<220> FEATURE:
<223> OTHER INFORMATION: primer

<400> SEQUENCE: 43
caggacaacc gccaaaaaga ttggcctc                                         28

<210> SEQ ID NO 44
<211> LENGTH: 28
<212> TYPE: DNA
<213> ORGANISM: Artificial Sequence
<220> FEATURE:
<223> OTHER INFORMATION: primer

<400> SEQUENCE: 44
gaggccaatc tttttggcgg ttgtcctg                                         28

<210> SEQ ID NO 45
<211> LENGTH: 28
<212> TYPE: DNA
<213> ORGANISM: Artificial Sequence
<220> FEATURE:
<223> OTHER INFORMATION: primer

<400> SEQUENCE: 45
cgagcaaacg atgtggaagg gctacagg                                         28

<210> SEQ ID NO 46
<211> LENGTH: 28
<212> TYPE: DNA
<213> ORGANISM: Artificial Sequence
<220> FEATURE:
<223> OTHER INFORMATION: primer

<400> SEQUENCE: 46
```

-continued tggctcaggc ggagtgagta cattgtcg                                          28

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
ccccacatcc ctgacaaggc tc                                                22

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
ctattcatgg tcgtcatcgt cc                                                22

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
tgagcgcgct ggtgacggcg ga                                                22

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
cttgatttgt aggcagcctt c                                                 21

<210> SEQ ID NO 51
<211> LENGTH: 22
<212> TYPE: DNA
<213> ORGANISM: Artificial Sequence
<220> FEATURE:
<223> OTHER INFORMATION: primer

<400> SEQUENCE: 51
atggaggagc acgactacga ct                                                22

<210> SEQ ID NO 52
<211> LENGTH: 23
<212> TYPE: DNA
<213> ORGANISM: Artificial Sequence
<220> FEATURE:
<223> OTHER INFORMATION: primer

<400> SEQUENCE: 52
tcctccatga tctgcttcct gta                                               23

<210> SEQ ID NO 53
<211> LENGTH: 24
<212> TYPE: DNA

```
<213> ORGANISM: Artificial Sequence
<220> FEATURE:
<223> OTHER INFORMATION: primer

<400> SEQUENCE: 53
gacgacgtgc ttcctgcggc tcaa                                              24

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
cttcctgcac cttcttcctg ta                                                22

<210> SEQ ID NO 55
<211> LENGTH: 19
<212> TYPE: DNA
<213> ORGANISM: Artificial Sequence
<220> FEATURE:
<223> OTHER INFORMATION: primer

<400> SEQUENCE: 55
atgtcgaggc tggccaggg                                                    19

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
catacgagga aattactgag gc                                                22

<210> SEQ ID NO 57
<211> LENGTH: 28
<212> TYPE: DNA
<213> ORGANISM: Artificial Sequence
<220> FEATURE:
<223> OTHER INFORMATION: primer

<400> SEQUENCE: 57
tctccaagct catgtggtcc gagggcta                                          28

<210> SEQ ID NO 58
<211> LENGTH: 28
<212> TYPE: DNA
<213> ORGANISM: Artificial Sequence
<220> FEATURE:
<223> OTHER INFORMATION: primer

<400> SEQUENCE: 58
tggagcacga aggtgaagaa gcccgagt                                          28

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
gcacggcaag gactacagcg                                                   20
```

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
cctgcctact tattcgaacg                                          20

<210> SEQ ID NO 61
<211> LENGTH: 21
<212> TYPE: DNA
<213> ORGANISM: Artificial Sequence
<220> FEATURE:
<223> OTHER INFORMATION: primer

<400> SEQUENCE: 61
agcaaggaca aggcgagcga g                                        21

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
cggcggtctt ctgcttggcg                                          20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
cctcgtgccc ctatcaactt                                          20

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
gacactaaag cgcccggtat                                          20

<210> SEQ ID NO 65
<211> LENGTH: 1077
<212> TYPE: DNA
<213> ORGANISM: Oryza sativa

<400> SEQUENCE: 65
atgccggcct tcgccgacat cgccatcgac ccgcctctgg ccgacagcta ccgcgcgctg      60
gcgctgctcc gccgcgaccg cgacggtggc attgcgccgc cggctgtgca gatggtcggc     120
tcgggcggcg ccgtgctgga gcgcgacctg ccgatggtgg acctggagcg gctgacgagg     180
ggcggcgcgg gggagaggaa ggcgtgcgcg gcgccatgg cgagggcggc gtcggagtgg     240
gggttcttcc agctgaccaa ccacggcgtg gccgggagc tgatggagga gatgaggcgg     300

```
gagcaggcaa ggctgttccg tctgccgttc gaaaccaagg agaaggccgg cctgctcaac    360
ggctcgtacc ggtggggcaa ccccaccgcc acgtcgctcc gccacctctc gtggtcggag    420
gcgttccacg tcccgctcgc cagcatctcc ggggcggatt gcgactttgg agacctcacc    480
tccttaaggg gcgtgatgca ggaggtggcc gaagcgatgt cgcgggtggc gaacacggtg    540
gcagcggcgc tggcggagga gctgaccggg cgcggaggcg gcggggcatc ggcggcgccg    600
tggttccctg cggggtgcga cgagacgacg tgcttcctgc ggctcaaccg gtacccggcg    660
tgccctttcg cggcggacac gttcgggctg gtgccgcaca cggacagcga ctttctcacc    720
gtcctgtgcc aggaccaggt cggggccctg cacctgatga aggactcccg gtgggtggcc    780
gtcaggccac gccccgacgc cctcgtcgtc aacatcggcg atctgtttca ggcgtggagc    840
aacaacaggt acaagagcgt ggagcataaa gtggtggcca acgccaagac ggaccggcta    900
tcggtggcct acttcctgtg cccgtcctac gactcgcttg tcgggacatg cggcgagcca    960
tcgccataca gggccttcac cttcggggag tacaggaaga aggtgcagga agacgtcagg   1020
acaaccggga aaagattgg cctcccaaac ttttcaagc attcttcagt acaataa       1077
```

<210> SEQ ID NO 66
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 66

Ser Tyr Arg Trp Gly Asn Pro Ser Ala Thr Ser Pro Ala Gln Tyr Ser
1               5                   10                  15
Val Ser Glu Ala Phe His Ile Ile Leu Ser Glu Val Ser Arg Gln Ser
            20                  25                  30
Glu His Asp Val Lys Glu Thr Gly Asp Lys Val Gly Leu Ser Arg Phe
        35                  40                  45
Leu Ile
    50

<210> SEQ ID NO 67
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 67

Ala Gly Ser Tyr Arg Trp Gly Thr Pro Ser Ala Thr Ser Ile Arg Gln
1               5                   10                  15
Leu Ser Trp Ser Glu Ala Phe His Val Pro Met Thr Asp Ile Ser Asp
            20                  25                  30
Gln Val Gln Glu Asp Val Lys Lys Phe Gly Phe Lys Val Gly Leu Pro
        35                  40                  45
Arg Phe Leu Asn
    50

<210> SEQ ID NO 68
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 68

```
Pro Gly Ser Tyr Arg Trp Gly Ser Pro Thr Pro Asn Cys Leu Ser Gln
1               5                   10                  15

Leu Ser Trp Ser Glu Ala Phe His Ile Pro Met Asn Asp Ile Cys Ser
                20                  25                  30

Gln Val Gln Gln Asp Val Arg Glu Phe Gly His Lys Ile Gly Leu Ser
            35                  40                  45

Arg Phe Leu Ile
        50
```

<210> SEQ ID NO 69
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 69

```
Ser Tyr Arg Trp Gly Thr Pro Thr Ala Lys Cys Leu Glu Gln Leu Ser
1               5                   10                  15

Trp Ser Glu Ala Tyr His Ile Pro Met Thr Thr Pro Arg Pro Gln Ile
                20                  25                  30

Met Glu Asp Val Arg Ser Thr Gly Arg Lys Ile Gly Leu His Arg Phe
            35                  40                  45

Arg Thr
    50
```

<210> SEQ ID NO 70
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 70

```
Ser Tyr Arg Trp Gly Asn Pro Thr Ala Thr Ser Leu Arg His Leu Ser
1               5                   10                  15

Trp Ser Glu Ala Phe His Val Pro Leu Ala Ser Ile Ser Gly Lys Val
                20                  25                  30

Gln Glu Asp Val Arg Thr Thr Gly Lys Lys Ile Gly Leu Pro Asn Phe
            35                  40                  45

Phe Lys
    50
```

<210> SEQ ID NO 71
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 71

```
Ser Tyr Arg Trp Gly Thr Pro Thr Ala Thr Ser Leu Arg Gln Leu Ser
1               5                   10                  15

Trp Ser Glu Ala Phe His Leu Pro Leu Ala Gly Ile Ser Gly Arg Val
                20                  25                  30

Gln Glu Asp Val Lys Lys Thr Gly Lys Lys Thr Gly Leu Ser Asn Phe
            35                  40                  45

Leu Val
    50
```

<210> SEQ ID NO 72
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 72

Ser Tyr Arg Trp Gly Asn Pro Thr Ala Thr Ser Leu Arg Gln Leu Ser
1               5                   10                  15

Trp Ser Glu Ala Phe His Val Pro Leu Ala Ser Ile Ser Gly Lys Val
            20                  25                  30

Gln Asp Asp Val Lys Arg Thr Gly Lys Lys Ile Gly Leu Pro Asn Phe
        35                  40                  45

Leu Lys
    50

<210> SEQ ID NO 73
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 73

Ser Tyr Arg Trp Gly Thr Pro Thr Ala Thr Ser Pro Ala Gln Leu Ser
1               5                   10                  15

Trp Ser Glu Ala Phe His Val Pro Leu Ala Ala Val Ser Gly Arg Val
            20                  25                  30

Gln Glu Asp Val Lys Lys Thr Gly Lys Lys Val Gly Leu Pro Gly Phe
        35                  40                  45

Leu Leu
    50

<210> SEQ ID NO 74
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 74

Ser Tyr Arg Trp Gly Ser Pro Thr Ala Thr Ser Pro Arg Gln Leu Ser
1               5                   10                  15

Trp Ser Glu Ala Phe His Val Pro Leu Ala Gly Ile Ser Gly Arg Val
            20                  25                  30

Gln Glu Asp Val Lys Lys Thr Gly Lys Lys Ile Gly Leu Pro Asn Phe
        35                  40                  45

Leu Leu
    50

<210> SEQ ID NO 75
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 75

Pro Tyr Arg Trp Gly Thr Pro Thr Ala Thr Arg Ser Lys His Phe Ser
1               5                   10                  15

```
Trp Ser Glu Ala Phe His Ile Pro Leu Thr Met Ile Ser Gln Ile
            20                  25                  30

Gln Glu Asp Val Lys Lys Ile Gly His Lys Ile Gly Leu Ser Arg Phe
        35                  40                  45

Leu Leu
    50

<210> SEQ ID NO 76
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 76

Ala Gly Ser Tyr Arg Trp Gly Ser Leu Asn Ala Thr Cys Ile Arg Gln
1               5                  10                  15

Leu Ser Trp Ser Glu Ala Glu His Ile Pro Leu Thr Asp Met Leu Gly
            20                  25                  30

Gln Val Arg Glu Asp Val His Asn Leu Gly Tyr Lys Ile Gly Leu Pro
        35                  40                  45

Lys Phe Leu Leu
    50

<210> SEQ ID NO 77
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 77

Ala Gly Ser Tyr Arg Trp Gly Thr Pro Ser Ala Thr Cys Ile Lys Gln
1               5                  10                  15

Leu Ser Trp Ser Glu Ala Phe His Ile Pro Leu Thr Asp Ile Leu Gly
            20                  25                  30

Gln Val Arg Asp Asp Val Gln Lys Leu Gly Ser Lys Ile Gly Leu Pro
        35                  40                  45

Arg Phe Leu Thr
    50

<210> SEQ ID NO 78
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 78

Ala Gly Ser Tyr Arg Trp Gly Thr Pro Thr Ala Thr Cys Ile Lys Gln
1               5                  10                  15

Leu Ser Trp Ser Glu Ala Phe His Ile Pro Leu Thr Asp Ile Leu Gly
            20                  25                  30

Gln Val Arg Asp Asp Val Gln Lys Leu Gly Ser Lys Ile Gly Leu Pro
        35                  40                  45

Arg Phe Ile Ile
    50

<210> SEQ ID NO 79
<211> LENGTH: 52
<212> TYPE: PRT
```

```
<213> ORGANISM: Artificial Sequence
<220> FEATURE:
<223> OTHER INFORMATION: Synthetic Polypeptide

<400> SEQUENCE: 79

Ser Gly Ser Tyr Arg Trp Gly Thr Pro Ser Ala Thr Cys Val Gly Gln
1               5                   10                  15

Leu Ser Trp Ser Glu Ala Phe His Ile Pro Leu Lys Asp Val Leu Glu
            20                  25                  30

Gln Val Arg Asp Asp Val Gln Lys Leu Gly Thr Lys Ile Gly Leu Pro
        35                  40                  45

Arg Phe Leu Leu
    50

<210> SEQ ID NO 80
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 80

Ser Tyr Arg Trp Gly Thr Pro Thr Ala Thr Cys Pro Asn Gln Phe Ser
1               5                   10                  15

Trp Ser Glu Ala Phe His Ile Pro Leu Thr Lys Ile Ser Glu Gln Val
            20                  25                  30

Arg Glu Asp Val Lys Thr Thr Gly His Lys Ile Gly Leu Pro Arg Phe
        35                  40                  45

Leu Leu
    50

<210> SEQ ID NO 81
<211> LENGTH: 51
<212> TYPE: PRT
<213> ORGANISM: Artificial Sequence
<220> FEATURE:
<223> OTHER INFORMATION: Synthetic Polypeptide

<400> SEQUENCE: 81

Ser Tyr Arg Trp Gly Ala Pro Thr Ala Ala Thr Ser Leu Arg His Leu
1               5                   10                  15

Ser Trp Ser Glu Ala Phe His Val Pro Leu Ala Ser Ile Ser Gly Lys
            20                  25                  30

Val Gln Glu Asp Val Lys Arg Thr Gly Arg Lys Ile Gly Leu Pro Asn
        35                  40                  45

Phe Leu Lys
    50

<210> SEQ ID NO 82
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 82

Ser Tyr Arg Trp Gly Thr Pro Thr Ala Thr Cys Pro Lys Glu Leu Ser
1               5                   10                  15

Trp Ser Glu Ala Phe His Ile Pro Leu Thr Lys Val Ser Glu Gln Val
            20                  25                  30

Gln Glu Asp Val Lys Lys Thr Gly His Lys Val Gly Leu Pro Arg Phe
```

```
<210> SEQ ID NO 83
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 83

Ser Tyr Arg Trp Gly Ala Pro Thr Ala Thr Ser Leu Arg His Leu Ser
1               5                   10                  15

Trp Ser Glu Ala Phe His Val Pro Leu Ala Ser Ile Ser Gly Lys Val
            20                  25                  30

Gln Glu Asp Val Lys Arg Thr Gly Arg Lys Ile Gly Leu Pro Asn Phe
        35                  40                  45

Leu Lys
    50

<210> SEQ ID NO 84
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 84

Ser Tyr Arg Trp Gly Thr Pro Thr Ala Thr Ser Leu Arg Gln Leu Ser
1               5                   10                  15

Trp Ser Glu Ala Phe His Ile Pro Leu Thr Ile Ser Gly Gln Val Gln
            20                  25                  30

Glu Asp Val Lys Lys Thr Gly Lys Ile Gly Leu Pro Arg Phe Leu Leu
        35                  40                  45
```